(12) United States Patent
Bogue et al.

(10) Patent No.: US 8,956,685 B2
(45) Date of Patent: Feb. 17, 2015

(54) USE OF DAMS TO IMPROVE YIELD IN FILM PROCESSING

(75) Inventors: Beuford A. Bogue, New Carlisle, IN (US); Alexander Mark Schobel, Whitehouse Station, NJ (US); Keith J. Kendall, Bridgewater, NJ (US)

(73) Assignee: Monosol RX, LLC, Warren, NJ (US)

( * ) Notice: Subject to any disclaimer, the term of this patent is extended or adjusted under 35 U.S.C. 154(b) by 828 days.

(21) Appl. No.: 12/711,883

(22) Filed: Feb. 24, 2010

(65) Prior Publication Data

US 2011/0206851 A1    Aug. 25, 2011

(51) Int. Cl.
*A61K 9/70*    (2006.01)

(52) U.S. Cl.
CPC .................................. *A61K 9/7007* (2013.01)
USPC .......................... 427/2.31; 427/275; 264/212

(58) Field of Classification Search
CPC .................................................... A61K 9/7007
USPC ....................... 427/275, 2.31, 2.28; 424/449; 264/212–213, 216
See application file for complete search history.

(56) References Cited

U.S. PATENT DOCUMENTS

| | | | | |
|---|---|---|---|---|
| 4,714,655 A | * | 12/1987 | Bordoloi et al. | 428/345 |
| 5,688,520 A | * | 11/1997 | Karsenty et al. | 424/434 |
| 6,716,017 B2 | * | 4/2004 | Papadopoulas | 425/194 |
| 6,808,739 B2 | * | 10/2004 | Sitz et al. | 427/2.31 |
| 7,115,507 B2 | | 10/2006 | Kawase | |
| 7,241,411 B2 | * | 7/2007 | Berry et al. | 264/160 |
| 2002/0110585 A1 | * | 8/2002 | Godbey et al. | 424/449 |
| 2004/0091677 A1 | | 5/2004 | Topolkaraev | |
| 2008/0102192 A1 | * | 5/2008 | Johnson et al. | 427/2.1 |
| 2009/0146336 A1 | | 6/2009 | Masi | |

FOREIGN PATENT DOCUMENTS

WO    2009027625 A2    3/2009
WO    WO 2009027625 A2 *   3/2009

OTHER PUBLICATIONS

International Search Report & Written Opinion for PCT/US11/25805, dated May 16, 2011.

* cited by examiner

*Primary Examiner* — Alex A Rolland
(74) *Attorney, Agent, or Firm* — Hoffmann & Baron, LLP

(57) ABSTRACT

The present invention relates to methods for forming films. In particular, the present invention relates to the formation of films on a substrate, the substrate having at least one dam portion.

51 Claims, 12 Drawing Sheets

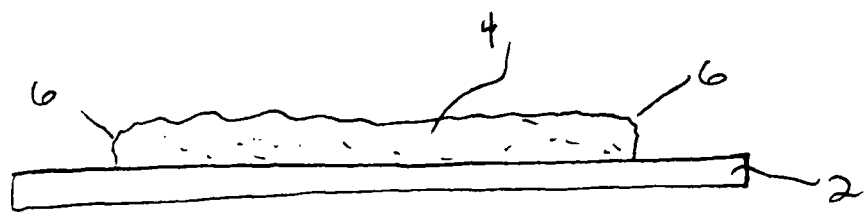
Fig 1A - Prior Art
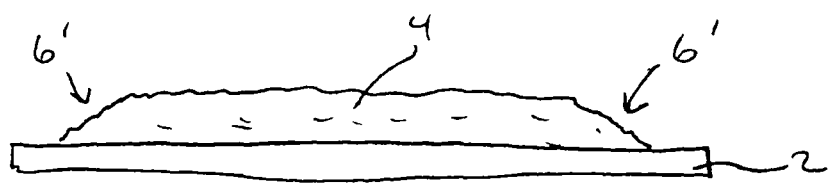
Fig 1B - Prior Art

USE OF DAMS TO IMPROVE YIELD IN FILM PROCESSING

FIELD OF THE INVENTION

The present invention relates to methods for forming films. In particular, the present invention relates to the formation of films on a substrate, the substrate having at least one dam portion.

BACKGROUND OF THE INVENTION

The use of films for the administration of active agents, such as pharmaceuticals, cosmetic and other materials, is becoming increasingly popular. Such films should have a fairly uniform size, and a substantially uniform distribution of components. The substantially uniform distribution of components is quite important when the films include pharmaceutical components, to ensure accurate dosages.

Films may be formed in any desired fashion, and in some cases it may be useful to form a film on the surface of a substrate. The use of a substrate to form film not only provides ease in processing but may also aid in packaging the film products. Typically, a wet film matrix is deposited onto the surface of a substrate, and then dried to form the resulting film. However, it has been found that traditional methods of forming a film on a substrate are unacceptable, as the wet film matrix has a tendency to "bleed out" the sides, therefore providing non-uniform edges. Non-uniform edges are undesirable since they are not uniform with the center portion of the film, and, in many instances, must be trimmed and discarded, creating wasted product. Attempts to prevent this lack of uniformity include forming films in pre-sized wells, which are very restrictive and do not allow for large-scale bulk processing of films.

The present invention seeks to solve the problems incurred with traditional film processing, such as by providing a method that reduces or altogether eliminates the bleed out problems incurred with other methods.

SUMMARY OF THE INVENTION

In one embodiment of the present invention, there is provided a method of forming a film product, including the steps of: providing a non-embossed substrate; embossing the non-embossed substrate to provide an embossed substrate having at least one confined region having a top surface; depositing a wet film matrix on the top surface of the confined region; and drying the wet film matrix on the embossed substrate to form a dried film.

In another embodiment of the present invention, there is provided a method of forming a film product, including the steps of: providing a substrate having at least one confined region having a top surface; depositing a wet film matrix on the top surface of the confined region; and drying the wet film matrix on the embossed substrate to form a dried film.

In other embodiments, there may be provided a substrate for forming a film product including at least one confined region, the confined region including a top surface and at least one dam.

In still another embodiment, there is provided a method of continuously forming a film product, including the steps of: providing a non-embossed substrate having a starting edge; feeding the starting edge of the non-embossed substrate into a film-forming mechanism, such that the non-embossed substrate continuously moves through the film-forming mechanism; continuously embossing the non-embossed substrate as it moves through the film-forming mechanism to provide an embossed substrate having at least one confined region having a top surface; continuously depositing a wet film matrix on the top surface of the confined region as the embossed substrate moves through the film-forming mechanism; and drying the wet film matrix on the embossed substrate to form a dried film.

BRIEF DESCRIPTION OF THE FIGURES

FIGS. 1A-1B depict prior methods of coating of a wet film matrix onto a planar substrate.

DETAILED DESCRIPTION OF THE INVENTION

Figure 2A:
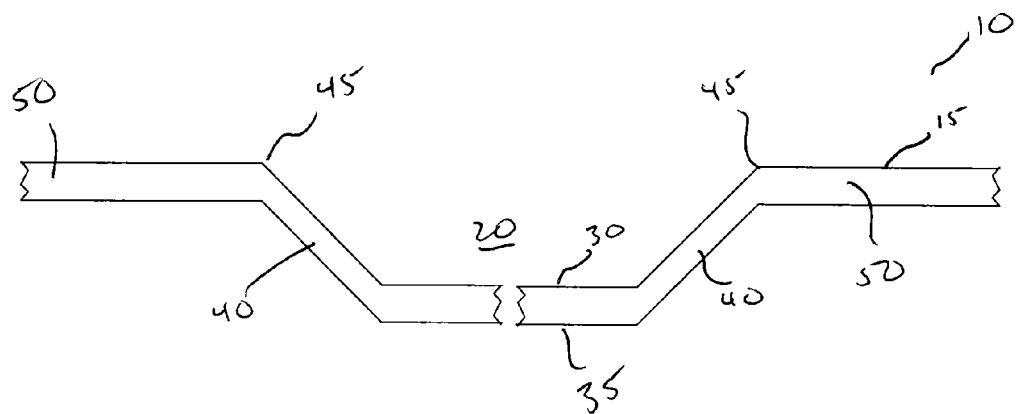
FIGS. 2A-2F depict various substrate dam formations useful in the present invention.

The present invention relates to methods of forming film. Specifically, the invention relates to methods of forming film on a substrate, while maintaining the uniformity of content and the structural integrity of the film product. Film systems embody a field of technology that has major advantages in areas of administering drug, medicament, and various other active and agent delivery systems to an individual in need thereof. In order to provide a desirable final product that exhibits advantageous characteristics and desirable properties, including uniformity of content, the processing and manufacturing of film strips and film technology is technologically demanding and cumbersome.

As used herein, the terms "pharmaceutical", "medicament", "drug" and "active" may be used interchangeably, and refer to a substance or composition useful for the prevention or treatment of a condition. The terms may include pharmaceuticals, neutraceuticals, cosmetic agents, biologic agents, bioeffective substances, and the like.

It will be understood that the term "film" includes delivery systems of any thickness, including films, sheets, discs, wafers, and the like, in any shape, including rectangular, square, or other desired shape. The film may be in the form of a continuous roll of film or may be sized to a desired length and width. The films described herein may be any desired thickness and size suitable for the intended use. For example, a film of the present invention may be sized such that it may be placed into the oral cavity of the user. Other films may be sized for application to the skin of the user, i.e., a topical use. For example, some films may have a relatively thin thickness of from about 0.1 to about 10 mils, while others may have a somewhat thicker thickness of from about 10 to about 30 mils. For some films, especially those intended for topical use, the thickness may be even larger, i.e., greater than about 30 mils. In addition, the term "film" includes single-layer compositions as well as multi-layer compositions, such as laminated films, coatings on films and the like. The composition in its dried film form maintains a uniform distribution of components through the application of controlled drying of the film. Films may include a pouch or region of medicament between two films.

In some embodiments of the invention, the films are intended for oral administration. In other embodiments, the films are intended for topical administration. As used herein, the term "topical agent" is meant to encompass active agents that are applied to a particular surface area. For example, in one embodiment, a topical agent is applied to an area of the skin. In other embodiments, the topical agent may also be applied to mucosal areas of the body, such as the oral (e.g., buccal, sublingual, tongue), vaginal, ocular and anal areas of the body. In other embodiments, a topical agent is applied to a hard surface, such as a particular surface area in need of treatment.

The medicament may be dispersed throughout the film, or it may be deposited onto one or more surfaces of the film. In either way, it is desirable that the amount of medicament per unit area is substantially uniform throughout the film. It is desired that the films of the present invention include a uniformity of component distribution throughout the volume of a given film. Such uniformity includes a substantially uniform amount of medicament per unit volume of the film, whether the medicament is within the matrix of the film or coated, laminated, or stabilized on one or more surfaces thereof. When such films are cut into individual units, the amount of the agent in the unit can be known with a great deal of accuracy. For the films formed herein, it is understood by one of ordinary skill in the art that the resulting film is not required to be 100% uniform. All that is required is that the film be substantially uniform—a slight amount of non-uniformity is understood to be acceptable. "Substantially uniform" may include, for example, a film that is about 90% uniform in content from one region of the film to another, or a film that is about 95% uniform in content from one region of the film to another, and most desirably about 99% uniform in content from one region of the film to another.

Uniformity of medicament throughout the film is important in administering an accurate and effective dose of medicament to a user. Various methods of forming uniform films, as well as various polymers, additives and fillers, may be used, including those methods and materials described in U.S. Pat. Nos. 7,425,292 and 7,357,891 and U.S. Publication No. 2005/0037055, which are herein incorporated by reference in their entireties. Any number of active components or pharmaceutical agents may be included in the films discussed herein.

Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (commercially available as Oxycontin®); ibuprofen (commercially available as Motrin®, Advil®, Motrin Children's®, Motrin IB®), Advil Children's®, Motrin Infants'®, Motrin Junior®, Ibu-2®, Proprinal®, Ibu-200®, Midol Cramp Formula®, Bufen®, Motrin Migraine Pain®, Addaprin® and Haltran®), aspirin (commercially available as Empirin®, Ecotrin®, Genuine Bayer®, and Halfprin®), acetaminophen (commercially available as Silapap Infant's®, Silapap Children's®, Tylenol®, Tylenol Children's®, Tylenol Extra Strength®, Tylenol Infants' Original®, Tylenol Infants'®, Tylenol Arthritis®, T-Painol®, Q-Pap®, Cetafen®, Dolono®, Tycolene®, APAP® and Aminofen®), and combinations thereof that may optionally include caffeine. Other pain relieving agents may be used in the present invention, including meperidine hydrochloride (commercially available as Demerol®), hydromorphone hydrochloride (commercially available as Dilaudid®), propoxyphene napsylate and acetaminophen (commercially available as Darvocet-N®), Fentanyl (commercially available as Duragesic® and Fentora®), sodium hyaluronate (commercially available as Euflexxa®), adalimumab (commercially available as Humira®), sumatriptan succinate (commercially available as Imitrex®), fentanyl iontophoretic (commercially available as Ionsys®), orphenadrine citrate (commercially available as Norgesic®), magnesium salicylate tetrahydrate (commercially available as Novasal®), oxymorphone hydrochloride (commercially available as Opana ER®), methocarbamol (commercially available as Robaxin®), carisoprodol (commercially available as Soma®), tramadol hydrochloride (commercially available as Ultracet® and Ultram®), morphine sulfate (commercially available as MS Contin®), metaxalone (commercially available as Skelaxin®), oxycodone hydrochloride (commercially available as OxyContin®), acetaminophen/oxycodone hydrochloride (commercially available as Percocet®), oxycodone/aspirin (commercially available as Percodan®), hydrocodone bitartrate/acetaminophen (commercially available as Vicodin®), hydrocodone bitartrate/ibuprofen (commercially available as Vicoprofen®), nepafenac (commercially available as Nevanac®), and pregabalin (commercially available as Lyrica®).

The present invention may further include agents such as NSAIDs, including etodolac (commercially available as Lodine®), ketorolac tromethamine (commercially available as Acular®), naproxen sodium (commercially available as Anaprox®, Naprosyn®), flurbiprofen (commercially available as Ansaid®), diclofenac sodium/misoprostol (commercially available as Arthrotec®), celecoxib (commercially available as Celebrex®), sulindac (commercially available as Clinoril®), oxaprozin (commercially available as Daypro®), piroxicam (commercially available as Feldene®), indomethacin (commercially available as Indocin®), meloxicam (commercially available as Mobic®), mefenamic acid (commercially available as Ponstel®), tolmetin sodium (commercially available as Tolectin®), choline magnesium trisalicylate (commercially available as Trilisate®), diclofenac sodium (commercially available as Voltaren®), and misoprostol (commercially available as Cytotec®). Opiate agonists and antagonists, such as buprenorphine and naloxone are further examples of drugs for use in the present invention.

Other preferred drugs for other preferred active ingredients for use in the present invention include anti-diarrheals such as loperamide (commercially available as Imodium AD®, Imotil®, Kaodene®, Imperim®, Diamode®, QC Anti-Diarrheal®, Health Care America Anti-Diarrheal®, Leader A-D®, and Imogen®), nitazoxanide (commercially available as Alinia®) and diphenoxylate hydrochloride/atropine sulfate (commercially available as Lomotil®), anti-histamines, anti-tussives, decongestants, vitamins, and breath fresheners. Common drugs used alone or in combination for colds, pain, fever, cough, congestion, runny nose and allergies, such as acetaminophen, ibuprofen, chlorpheniramine maleate, dextromethorphan, dextromethorphan HBr, phenylephrine HCl, pseudoephedrine HCl, diphenhydramine and combinations thereof, such as dextromethophan HBr and phenylephrine HCl (available as Triaminic®) may be included in the film compositions of the present invention.

Other active agents useful in the present invention include, but are not limited to alcohol dependence treatment, such as acamprosate calcium (commercially available as Campral®); Allergy treatment medications, such as promethazine hydrochloride (commercially available as Phenergan®), hydrocodone polistirex/chlorpheniramine polistirex (commercially available as Tussionex®), cetirizine hydrochloride (commercially available as Zyrtec®), cetirizine hydrochloride/pseudoephedrine hydrochloride (commercially available as Zyrtec-D®), promethazine hydrochloride/codeine phosphate (commercially available as Phenergan® with Codeine), pemirolast (commercially available as Alamast®), fexofenadine hydrochloride (commercially available as Allegra®), meclizine hydrochloride (commercially available as Antivert®), azelastine hydrochloride (commercially available as Astelin®), nizatidine (commercially available as Axid®), desloratadine (commercially available as Clarinex®), cromolyn sodium (commercially available as Crolom®), epinastine hydrochloride (commercially available as Elestat®), azelastine hydrochloride (commercially available as Optivar®), prednisolone sodium phosphate (commercially available as Orapred ODT®), olopatadine hydrochloride (commercially available as Patanol®), ketotifen fumarate (commercially available as Zaditor®), and montelukast sodium (commercially available as Singulair®); and anti-histamines such as diphenhydramine HCl (available as Benadryl®), loratadine (available as Claritin®), astemizole (available as Hismanal®), nabumetone (available as Relafen®), diphenydramine HCL (available as TheraFlu®) and clemastine (available as Tavist®).

Films of the present invention may further include Alzheimer's treatment medications, such as tacrine hydrochloride (commercially available as Cognex®), galantamine (commercially available as Razadyne®), donepezil hydrochloride (commercially available as Aricept®), rivastigmine tartrate (commercially available as Exelon®), and memantine (commercially available as Namenda®); anemia medication, such as cyanocobalamin (commercially available as Nascobal®); anesthetics, such as antipyrine with benzocaine (commercially available as Auralgan®, Aurodex® and Auroto®); angina medication, such as amlodipine besylate (commercially available as Norvasc®), nitroglycerin (commercially available as Nitro-Bid®, Nitro-Dur®, Nitrolingual®, Nitrostat®, Transderm-Nitro®), isosorbide mononitrate (commercially available as Imdur®), and isosorbide dinitrate (commercially available as Isordil®); anti-tussives such as guaifensin; anti-Alzheimer's agents, such as nicergoline; and $Ca^H$-antagonists such as nifedipine (commercially available as Procardia® and Adalat®).

Actives useful in the present invention may also include anti-asthmatics, such as albuterol sulfate (commercially available as Proventil®), ipratropium bromide (commercially available as Atrovent®), salmeterol xinafoate (commercially available as Serevent®), zafirlukast (commercially available as Accolate®), flunisolide (commercially available as AeroBid®), metaproterenol sulfate (commercially available as Alupent®), albuterol inhalation (commercially available as Ventolin®), terbutaline sulfate (commercially available as Brethine®), formoterol (commercially available as Foradil®), cromolyn sodium (commercially available as Intal®), levalbuterol hydrochloride (commercially available as Xopenex®), zileuton (commercially available as Zyflo®), fluticasone propionate/salmeterol (commercially available as Advair®), albuterol sulfate/triamcinolone acetonide (commercially available as Azmacort®), dimethylxanthine (commercially available as Theophylline®), and beclomethasone (commercially available as Beclovent®, Beconase®, Qvar®, Vancenase®, Vanceril®); and antibacterial medications, such as trimethoprim/sulfamethoxazole (commercially available as Bactrim®), mupirocin (commercially available as Bactroban®), metronidazole (commercially available as Flagyl®), sulfisoxazole acetyl (commercially available as Gantrisin®), bismuth subsalicylate and metronidazole/tetracycline hydrochloride (commercially available as Helidac Therapy®), nitrofurantoin (commercially available as Macrodantin®), norfloxacin (commercially available as Noroxin®), erythromycin ethylsuccinate/Sulfisoxazole acetyl (commercially available as Pediazole®), and levofloxacin (commercially available as Levaquin®).

The present invention may further include one or more Antibiotics, including amoxicillin (commercially available as Amoxil®), ampicillin (commercially available as Omnipen®, Polycillin® and Principen®), amoxicillin/clavulanate potassium (commercially available as Augmentin®), moxifloxacin hydrochloride (commercially available as Avelox®), clarithromycin (commercially available as Biaxin®), ceftibuten (commercially available as Cedax®), cefuroxime axetil (commercially available as Ceftin®), cefprozil (commercially available as Cefzil®), ciprofloxacin hydrochloride (commercially available as Ciloxan® and Cipro®), clindamycin phosphate (commercially available as Cleocin T®), doxycycline hyclate (commercially available as Doryx®), dirithromycin (commercially available as Dynabac®), erythromycin (commercially available as E.E.S.®, E-Mycin®, Eryc®, Ery-Tab®, Erythrocin®, and PCE®), erythromycin topical (commercially available as A/T/S®, Erycette®, T-Stat®), gemifloxacin (commercially available as Factive®), ofloxacin (commercially known as Ocuflox®, Floxin®), telithromycin (commercially available as Ketek®), lomefloxacin hydrochloride (commercially available as Maxaquin®), minocycline hydrochloride (commercially available as Minocin®), fosfomycin tromethamine (commercially available as Monurol®), penicillin with potassium (commercially available as Penicillin VK®, Veetids®), trimethoprim (commercially available as Primsol®), ciprofloxacin hydrochloride (commercially available as Proquin XR®), rifampin, isoniazid and pyrazinamide (commercially available as Rifater®), cefditoren (commercially available as Spectracef®), cefixime (commercially available as Suprax®), tetracycline (commercially available as Achromycin V® and Sumycin®), tobramycin (commercially available as Tobrex®), rifaximin (commercially available as Xifaxan®), azithromycin (commercially available as Zithromax®), azithromycin suspension (commercially available as Zmax®), linezolid (commercially available as Zyvox®), benzoyl peroxide and clindamycin (commercially available as BenzaClin®), erythromycin and benzoyl peroxide (commercially available as Benzamycin®), ciprofloxacin and dexamethasone (commercially available as Ciprodex®), polymyxin B sulfate/neomycin sulfate/hydrocortisone (commercially available as Cortisporin®), colistin sulfate/neomycin sulfate/hydrocortisone acetate/thonzonium bromide (commercially available as Cortisporin-TC Otic®), cephalexin hydrochloride (commercially available as Keflex®), cefdinir (commercially available as Omnicef®), and gatifloxacin (commercially available as Zymar®).

Other useful actives include cancer treatment medications, including cyclophosphamide (commercially available as Cytoxan®), methotrexate (commercially available as Rheumatrex® and Trexal®), tamoxifen citrate (commercially available as Nolvadex®), and anastrozole (commercially available as Arimidex®); anti-coagulants, such as aspirin with extended-release dipyridamole (commercially available as Aggrenox®), warfarin sodium (commercially available as Coumadin®), dipyridamole (commercially available as Persantine®), dalteparin (commercially available as Fragmin®), danaparoid (commercially available as Orgaran®), enoxaparin (commercially available as Lovenox®), heparin (commercially available as Hep-Lock, Hep-Pak, Hep-Pak CVC, Heparin Lock Flush), tinzaparin (commercially available as Innohep®), and clopidogrel bisulfate (commercially available as Plavix®); antiemetics, such as granisetron hydrochloride (commercially available as Kytril®) and nabilone (commercially available as Cesamet®), trimethobenzamide hydrochloride (commercially available as Tigan®), and ondansetron hydrochloride (commercially available as Zofran®); anti-fungal treatment, such as ketoconazole (commercially available as Nizoral®), posaconazole (commercially available as Noxafil®), ciclopirox (commercially available as Penlac®), griseofulvin (commercially available as Gris-PEG®), oxiconazole nitrate (commercially available as Oxistat®), fluconazole (commercially available as Diflucan®), sertaconazole nitrate (commercially available as Ertaczo®), terbinafine hydrochloride (commercially available as Lamisil®), ciclopirox (commercially available as Loprox®), nystatin/triamcinolone acetonide (commercially available as Mycolog-II®), econazole nitrate (commercially available as Spectazole®), itraconazole (commercially available as Sporanox®), and terconazole (commercially available as Terazol®).

Active agents may further include anti-inflammatory medications, such as hydroxychloroquine sulfate (commercially available as Plaquenil®), fluticasone propionate (commercially available as Cutivate®), amcinonide (commercially available as Cyclocort®), methylprednisolone (commercially available as Medrol®), budesonide (commercially available as Entocort EC®), anakinra (commercially available as Kineret®), diflorasone diacetate (commercially available as Psorcon®), and etanercept (commercially available as Enbrel®); antispasmodic medication, such as phenobarbital/hyoscyamine sulfate/atropine sulfate/scopolamine hydrobromide (commercially available as Donnatal®); antiviral treatment, such as oseltamivir phosphate (commercially available as Tamiflu®); anti-parasites medication, including tinidazole (commercially available as Tindamax®); appetite treatment mediations, such as megestrol acetate (commercially available as Megace ES®), phentermine hydrochloride (commercially available as Adipex-P®), and diethylpropion hydrochloride (commercially available as Tenuate®); arthritis medications, including leflunomide (commercially available as Arava®); bladder control medication, such as trospium chloride (commercially available as Sanctura®), desmopressin acetate (commercially available as DDAVP®), tolterodine tartrate (commercially available as Detrol®), oxybutynin chloride (commercially available as Ditropan®), darifenacin (commercially available as Enablex®), and solifenacin succinate (commercially available as VESIcare®); blood vessel constrictors, such as methylergonovine maleate (commercially available as Methergine®); cholesterol lowering medication, including paricalcitol (commercially available as Altocor®), lovastatin, niacin (commercially available as Advicor®), colestipol hydrochloride (commercially available as Colestid®), rosuvastatin calcium (commercially available as Crestor®), fluvastatin sodium (commercially available as Lescol®), atorvastatin calcium (commercially available as Lipitor®), lovastatin (commercially available as Mevacor®), niacin (commercially available as Niaspan®), pravastatin sodium (commercially available as Pravachol®), pavastatin sodium with buffered aspirin (commercially available as Pravigard PAC®), cholestyramine (commercially available as Questran®), simvastatin and niacin (commercially available as Simcor®), atenolol, chlorthalidone (commercially available as Tenoretic®), atenolol (commercially available as Tenormin®), fenofibrate (commercially available as Tricor®), fenofibrate (commercially available as Triglide®), ezetimibe/simvastatin (commercially available as Vytorin®), colesevelam (commercially available as WelChol®), bisoprolol fumarate (commercially available as Zebeta®), ezetimibe (commercially available as Zetia®), bisoprolol fumarate/hydrochlorothiazide (commercially available as Ziac®), and simvastatin (commercially available as Zocor®).

The actives included herein may also include chronic kidney disease medication, such as paricalcitol (commercially available as Zemplar®); contraceptive agents, including etonogestrel (commercially available as Implanon®), norethindrone acetate, ethinyl estradiol (commercially available as Loestrin 24 FE®), ethinyl estradiol, norelgestromin (commercially available as Ortho Evra®), levonorgestrel (commercially available as Plan B®), levonorgestrel and ethinyl estradiol (commercially available as Preven®), levonorgestrel, ethinyl estradiol (commercially available as Seasonique®), and medroxyprogesterone acetate (commercially available as Depo-Provera®); COPD medication, such as arformoterol tartrate (commercially available as Brovana®) and ipratropium bromide, albuterol sulfate (commercially available as Combivent®); cough suppressants, including benzonatate (commercially available as Tessalon®), guaifenesin, codeine phosphate (commercially available as Tussi-Organidin NR®), and acetaminophen, codeine phosphate (commercially available as Tylenol with Codeine®); medication for the treatment of diabetes, including pioglitazone hydrochloride, metformin hydrochloride (commercially available as ACTOplus Met®), pioglitazone hydrochloride (commercially available as Actos®), glimepiride (commercially available as Amaryl®), rosiglitazone maleate, metformin hydrochloride (commercially available as Avandamet®), rosiglitazone maleate (commercially available as Avandaryl®), rosiglitazone maleate (commercially available as Avandia®), exenatide (commercially available as Byetta®), chlorpropamide (commercially available as Diabinese®), pioglitazone hydrochloride, glimepiride (commercially available as Duetact®), metformin hydrochloride (commercially available as Glucophage®), glipizide (commercially available as Glucotrol®), glyburide, metformin (commercially available as Glucovance®), metformin hydrochloride (commercially available as Glumetza®), sitagliptin (commercially available as Januvia®), detemir (commercially available as Levemir®), glipizide, metformin hydrochloride (commercially available as Metaglip®), glyburide (commercially available as Micronase®), repaglinide (commercially available as Prandin®), acarbose (commercially available as Precose®), nateglinide (commercially available as Starlix®), pramlintide acetate (commercially available as Symlin®), and tolazamide (commercially available as Tolinase®).

Other useful agents of the present invention may include digestive agents, such as sulfasalazine (commercially available as Azulfidine®), rabeprazole sodium (commercially available as AcipHex®), lubiprostone (commercially available as Amitiza®), dicyclomine hydrochloride (commercially available as Bentyl®), sucralfate (commercially available as Carafate®), lactulose (commercially available as Chronulac®), docusate (commercially available as Colace®), balsalazide disodium (commercially available as Colazal®), losartan potassium (commercially available as Cozaar®), olsalazine sodium (commercially available as Dipentum®), chlordiazepoxide hydrochloride, clidinium bromide (commercially available as Librax®), esomeprazole magnesium (commercially available as Nexium®), famotidine (commercially available as Pepcid®), lansoprazole (commercially available as Prevacid®), lansoprazole and naproxen (commercially available as Prevacid NapraPAC®), amoxicillin/clarithromycin/lansoprazole (commercially available as Prevpac®), omeprazole (commercially available as Prilosec®), pantoprazole sodium (commercially available as Protonix®), metoclopramide hydrochloride (commercially available as Reglan®), cimetidine (commercially available as Tagamet®), ranitidine hydrochloride (commercially available as Zantac®), and omeprazole, sodium bicarbonate (commercially available as Zegerid®); diuretics, including spironolactone, hydrochlorothiazide (commercially available as Aldactazide®), spironolactone (commercially available as Aldactone®). bumetanide (commercially available as Bumex®), torsemide (commercially available as Demadex®), chlorothiazide (commercially available as Diuril®), furosemide (commercially available as Lasix®), metolazone (commercially available as Zaroxolyn®), and hydrochlorothiazide, triamterene (commercially available as Dyazide®).

Agents useful herein may also include treatment for emphysema, such as tiotropium bromide (commercially available as Spiriva®); enema treatments, including aminosalicylic acid (commercially available as Mesalamine® and Rowasa®); epilepsy medications, including valproic acid (commercially available as Depakene®), felbamate (commercially available as Felbatol®), lamotrigine (commercially available as Lamictal®), primidone (commercially available as Mysoline®), oxcarbazepine (commercially available as Trileptal®), zonisamide (commercially available as Zonegran®), levetiracetam (commercially available as Keppra®), and phenytoin sodium (commercially available as Dilantin®).

Erectile dysfunction therapies useful herein include, but are not limited to, drugs for facilitating blood flow to the penis, and for effecting autonomic nervous activities, such as increasing parasympathetic (cholinergic) and decreasing sympathetic (adrenersic) activities. Useful agents for treatment of erectile dysfunction include, for example, those agents available as alprostadil (commercially available as Caverject®), tadalafil (commercially available as Cialis®), vardenafil (commercially available as Levitra®), apomorphine (commercially available as Uprima®), yohimbine hydrochloride (commercially available as Aphrodyne®, Yocon®), and sildenafil citrate (commercially available as Viagra®).

Agents useful herein may further include eye medications and treatment, such as dipivefrin hydrochloride (commercially available as Propine®), valganciclovir (commercially available as Valcyte®), bromfenac (commercially available as Xibrom®), fluorometholone (commercially available as FML®), pilocarpine hydrochloride (commercially available as Pilocar®), cyclosporine (commercially available as Restasis®), brimonidine tartrate (commercially available as Alphagan P®), dorzolamide hydrochloride/timolol maleate (commercially available as Cosopt®), bimatoprost (commercially available as Lumigan®), timolol maleate (available as Timoptic®), travoprost (commercially available as Travatan®), latanoprost (commercially available as Xalatan®), echothiophate iodide (commercially available as Phospholine Iodide®), and ranibizumab (commercially available as Lucentis®); fluid controllers, such as acetazolamide (commercially available as Diamox®); gallstone medications, including ursodiol (commercially available as Actigall®); medication for the treatment of gingivitis, including chlorhexidine gluconate (commercially available as Peridex®); headache medications, including butalbital/codeine phosphate/aspirin/caffeine (commercially available as Fiornal® with Codeine), naratriptan hydrochloride (commercially available as Amerge®), almotriptan (commercially available as Axert®), ergotamine tartrate/caffeine (commercially available as Cafergot®), butalbital/acetaminophen/caffeine (commercially available as Fioricet®), butalbital/aspirin/caffeine (commercially available as Fiorinal®), frovatriptan succinate (commercially available as Frova®), rizatriptan benzoate (commercially available as Maxalt®), isometheptene mucate/dichloralphenazone/acetaminophen (commercially available as Midrin®), dihydroergotamine mesylate (commercially available as Migranal®), eletriptan hydrobromide (commercially available as Relpax®), and zolmitriptan (commercially available as Zomig®); and heart treatments, including quinidine sulfate, isosorbide dinitrate/hydralazine hydrochloride (commercially available as BiDil®), digoxin (commercially available as Lanoxin®), flecainide acetate (commercially available as Tambocor®), mexiletine hydrochloride (commercially available as Mexitil®), disopyramide phosphate (commercially available as Norpace®), procainamide hydrochloride (commercially available as Procanbid®), and propafenone (commercially available as Rythmol®).

Other useful agents include hepatitis treatments, including entecavir (commercially available as Baraclude®), hepatitis B immune globulin (commercially available as HepaGam B®), and copegus/rebetol/ribasphere/vilona/virazole (commercially available as Ribavirin®); herpes treatments, including valacyclovir hydrochloride (commercially available as Valtrex®), penciclovir (commercially available as Denavir®), acyclovir (commercially available as Zovirax®), and famciclovir (commercially available as Famvir®); treatment for high blood pressure, including enaprilat (available as Vasotec®), captopril (available as Capoten®) and lisinopril (available as Zestril®), verapamil hydrochloride (available as Calan®), ramipril (commercially available as Altace®), olmesartan medoxomil (commercially available as Benicar®), amlodipine/atorvastatin (commercially available as Caduet®), nicardipine hydrochloride (commercially available as Cardene®), diltiazem hydrochloride (commercially available as Cardizem®), quinapril hydrochloride (commercially available as Accupril®), quinapril hydrochloride/hydrochlorothiazide (commercially available as Accuretic®), perindopril erbumine (commercially available as Aceon®), candesartan cilexetil (commercially available as Atacand®), candesartan cilexetil/hydrochlorothiazide (commercially available as Atacand HCT®), irbesartan/hydrochlorothiazide (commercially available as Avalide®), irbesartan (commercially available as Avapro®), amlodipine besylate/olmesartan medoxomil (commercially available as Azor®), levobunolol hydrochloride (commercially available as Betagan®), betaxolol hydrochloride (commercially available as Betoptic®), nebivolol (commercially available as Bystolic®), captopril/hydrochlorothiazide (commercially available as Capozide®), doxazosin mesylate (commercially available as Cardura®), clonidine hydrochloride (commercially available as Catapres®), carvedilol (commercially available as Coreg®), nadolol (commercially available as Corgard®), nadolol/bendroflumethiazide (commercially available as Corzide®), valsartan (commercially available as Diovan®), isradipine (commercially available as DynaCirc®), wytensin. (commercially available as Guanabenz Acetate®), tenex (commercially available as Guanfacine Hydrochloride®), losartan potassium/hydrochlorothiazide (commercially available as Hyzaar®), propranolol hydrochloride (commercially available as Indera®), propranolol hydrochloride/hydrochlorothiazide (commercially available as Inderide®), eplerenone (commercially available as Inspra®), ambrisentan (commercially available as Letairis®), enalapril maleate/felodipine (commercially available as Lexxel®), metoprolol tartrate (commercially available as Lopressor®), benazepril hydrochloride (commercially available as Lotensin®), benazepril hydrochloride/hydrochlorothiazide (commercially available as Lotensin HCT®), amlodipine/benazepril hydrochloride (commercially available as Lotrel®), indapamide (commercially available as Lozol®), trandolapril (commercially available as Mavik®), telmisartan (commercially available as Micardis®), telmisartan/hydrochlorothiazide (commercially available as Micardis HCT®), prazosin hydrochloride (commercially available as Minipress®), amiloride, hydrochlorothiazide (commercially available as Moduretic®), fosinopril sodium (commercially available as ZZXT Monopril®), fosinopril sodium/hydrochlorothiazide (commercially available as Monopril-HCT®), pindolol (commercially available as Visken®), felodipine (commercially available as Plendil®), sildenafil citrate (commercially available as Revatio®), Nisoldipine (commercially available as Sular®), trandolapril/verapamil hydrochloride (commercially available as Tarka®), aliskiren (commercially available as Tekturna®), eprosartan mesylate (commercially available as Teveten®), eprosartan mesylate/hydrochlorothiazide (commercially available as Teveten HCT®), moexipril hydrochloride/hydrochlorothiazide (commercially available as Uniretic®), moexipril hydrochloride (commercially available as Univasc®), enalapril maleate/hydrochlorothiazide (commercially available as Vaseretic®), and lisinopril/hydrochlorothiazide (commercially available as Zestoretic®).

The present invention may include agents useful in the medication for the treatment of HIV/AIDS, such as amprenavir (commercially available as Agenerase®), tipranavir (commercially available as Aptivus®), efavirenz/emtricitabine/tenofovir (commercially available as Atripla®), lamivudine/zidovudine (commercially available as Combivir®), indinavir sulfate (commercially available as Crixivan®), lamivudine (commercially available as Epivir®), saquinavir (commercially available as Fortovase®), zalcitabine (commercially available as Hivid®), lopinavir/ritonavir (commercially available as Kaletra®), fosamprenavir calcium (commercially available as Lexiva®), ritonavir (commercially available as Norvir®), zidovudine (commercially available as Retrovir®), atazanavir sulfate (commercially available as Reyataz®), efavirenz (commercially available as Sustiva®), abacavir/lamivudine/zidovudine (commercially available as Trizivir®), didanosine (commercially available as Videx®), nelfinavir mesylate (commercially available as Viracept®), nevirapine (commercially available as Viramune®), tenofovir disoproxil fumarate (commercially available as Viread®), stavudine (commercially available as Zerit®), and abacavir sulfate (commercially available as Ziagen®); homocysteiene removers, including betaine anhydrous (commercially available as Cystadane®); medications, such as insulin (commercially available as Apidra®, Humalog®, Humulin®, Iletin®, and Novolin®); and HPV treatment, such as Human papillomavirus vaccine (commercially available as Gardasil®); immunosuppressants, including cyclosporine (commercially available as Gengraf®, Neoral®, Sandimmune®, and Apo-Cyclosporine®).

Agents useful in the present invention may further include prolactin inhibitors, such as bromocriptine mesylate (commercially available as Parlodel®); medications for aiding in stress tests, such as regadenoson (commercially available as Lexiscan®); baldness medication, including finasteride (commercially available as Propecia® and Proscar®); pancreatitis treatment, such as gemfibrozil (commercially available as Lopid®); hormone medications, such as norethindrone acetate/ethinyl estradiol (commercially available as femHRT®), goserelin acetate (commercially available as Zoladex®), progesterone gel (commercially available as Prochieve®), progesterone (commercially available as Prometrium®), calcitonin-salmon (commercially available as Miacalcin®), calcitriol (commercially available as Rocaltrol®), Synthroid (commercially available as Levothroid®, Levoxyl®, Unithroid®), testosterone (commercially available as Testopel®, Androderm®, Testoderm®, and Andro-Gel®); menopause medication, such as estradiol/norethindrone acetate (commercially available as Activella®), drospirenone/estradiol (commercially available as Angeliq®), estradiol/levonorgestrel (commercially available as Climara Pro®), estradiol/norethindrone acetate (commercially available as CombiPatch®), estradiol (commercially available as Estrasorb®, Vagifem® and EstroGel®), esterified estrogens and methyltestosterone (commercially available as Estratest®), estrogen (commercially available as Alora®, Climara®, Esclim®, Estraderm®, Vivelle®, Vivelle-Dot®), estropipate (commercially available as Ogen®), conjugated estrogens (commercially available as Premarin®), and medroxyprogesterone acetate (commercially available as Provera®); menstrual medications, including leuprolide acetate (commercially available as Lupron Depot), and norethindrone acetate (commercially available as Aygestin); and muscle relaxants, including cyclobenzaprine hydrochloride (commercially available as Flexeril®), tizanidine (commercially available as Zanaflex®), and hyoscyamine sulfate (commercially available as Levsin®).

Agents useful herein may also include osteoporosis medications, including ibrandronate sodium (commercially available as Boniva®), risedronate (commercially available as Actonel®), raloxifene hydrochloride (commercially available as Evista®, Fortical®), and alendronate sodium (commercially available as Fosamax®); ovulation enhancers, including clomiphene citrate (commercially available as Serophene®, Clomid®, Serophene®); Paget's disease treatment, such as etidronate disodium (commercially available as Didronel®); pancreatic enzyme deficiency medications, such as pancrelipase (commercially available as Pancrease®); medication for the treatment of Parkinson's disease, such as pramipexole dihydrochloride (commercially available as Mirapex®), ropinirole hydrochloride (commercially available as Requip®), carbidopa/levodopa (commercially available as Sinemet CR®), carbidopa/levodopa/entacapone (commercially available as Stalevo®), selegiline hydrochloride (commercially available as Zelapar®), rasagiline (commercially available as Azilect®), entacapone (commercially available as Comtan®), and selegiline hydrochloride (commercially available as Eldepryl®); prostate medication, including flutamide (commercially available as Eulexin®), nilutamide (commercially available as Nilandron®), dutasteride (commercially available as Avodart®), tamsulosin hydrochloride (commercially available as Flomax®), terazosin hydrochloride (commercially available as Hytrin®), and alfuzosin hydrochloride (commercially available as UroXatral®).

Films of the present invention may further include psychiatric medications, including alprazolam (available as Niravam®, Xanax®), clozopin (available as Clozaril®), haloperidol (available as Haldol®), fluoxetine hydrochloride (available as Prozac®), sertraline hydrochloride (available as Zoloft®), and paroxtine hydrochloride (available as Paxil®), aripiprazole (commercially aavialbe as Abilify®), Amphetamines and methamphetamines (commercially available as Adderall® and Desoxyn®), clomipramine hydrochloride (commercially available as Anafranil®), Buspirone hydrochloride (commercially available as BuSpar®), citalopram hydrobromide (commercially available as Celexa®), duloxetine hydrochloride (commercially available as Cymbalta®), methylphenidate (commercially available as Ritalin, Daytrana®), divalproex sodium (Valproic acid) (commercially available as Depakote®), dextroamphetamine sulfate (commercially available as Dexedrine®), venlafaxine hydrochloride (commercially available as Effexor®), selegiline (commercially available as Emsam®), carbamazepine (commercially available as Equetro®), lithium carbonate (commercially available as Eskalith®), fluvoxamine maleate/dexmethylphenidate hydrochloride (commercially available as Focalin®), ziprasidone hydrochloride (commercially available as Geodon®), ergoloid mesylates (commercially available as Hydergine®), escitalopram oxalate (commercially available as Lexapro®), chlordiazepoxide (commercially available as Librium®), molindone hydrochloride (commercially available as Moban®), phenelzine sulfate (commercially available as Nardil®), thiothixene (commercially available as Navane®), desipramine hydrochloride (commercially available as Norpramin®), benzodiazepines (such as those available as Oxazepam®), nortriptyline hydrochloride (commercially available as Pamelor®), tranylcypromine sulfate (commercially available as Parnate®), prochlorperazine, mirtazapine (commercially available as Remeron®), risperidone (commercially available as Risperdal®), quetiapine fumarate (commercially available as Seroquel®), doxepin hydrochloride (commercially available as Sinequan®), atomoxetine hydrochloride (commercially available as Strattera®), trimipramine maleate (commercially available as Surmontil®), olanzapine/fluoxetine hydrochloride (commercially available as Symbyax®), imipramine hydrochloride (commercially available as Tofranil®), protriptyline hydrochloride (commercially available as Vivactil®), bupropion hydrochloride (commercially available as Wellbutrin®, Wellbutrin SR®), and Wellbutrin XR®), and olanzapine (commercially available as Zyprexa®).

Agents useful herein may also include uric acid reduction treatment, including allopurinol (commercially available as Zyloprim®); seizure medications, including gabapentin (commercially available as Neurontin®), ethotoin (commercially available as Peganone®), and topiramate (commercially available as Topamax®); treatment for shingles, such as zoster vaccine live (commercially available as Zostavax®); skin care medications, including calcipotriene (commercially available as Dovonex®), isotretinoin (commercially available as Accutane®), hydrocortisone/iodoquinol (commercially available as Alcortin®), sulfacetamide sodium/sulfur (commercially available as Avar®), azelaic acid (commercially available as Azelex®, Finacea®), benzoyl peroxide (commercially available as Desquam-E®), adapalene (commercially available as Differin®), fluorouracil (commercially available as Efudex®), pimecrolimus (commercially available as Elidel®), topical erythromycin (commercially available as A/T/S®, Erycette®, T-Stat®), hydrocortisone (commercially available as Cetacort®, Hytone®, Nutracort®), metronidazole (commercially available as MetroGel®), doxycycline (commercially available as Oracea®), tretinoin (commercially available as Retin-A® and Renova®), mequinol/tretinoin (commercially available as Solagé®), acitretin (commercially available as Soriatane®), calcipotriene hydrate/betamethasone dipropionate (commercially available as Taclonex®), tazarotene (commercially available as Tazorac®), fluocinonide (commercially available as Vanos®), desonide (commercially available as Verdeso®), miconazole nitrate/Zinc oxide (commercially available as Vusion®), ketoconazole (commercially available as Xolegel®), and efalizumab (commercially available as Raptiva®).

Other agents useful herein may include Sleep disorder medications, including zaleplon (available as Sonata®) and eszopiclone (available as Lunesta®), zolpidem tartrate (commercially available as Ambient, Ambien CR®), lorazepam (commercially available as Ativan®), flurazepam hydrochloride (commercially available as Dalmane®), triazolam (commercially available as Halcion®), clonazepam (commercially available as Klonopin®), barbituates, such as Phenobarbital®), Modafinil (commercially available as Provigil®), temazepam (commercially available as Restoril®), ramelteon (commercially available as Rozerem®), clorazepate dipotassium (commercially available as Tranxene®), diazepam (commercially available as Valium®), quazepam (commercially available as Doral®), and estazolam (commercially available as ProSom®); smoking cessation medications, such as varenicline (commercially available as Chantix®), nicotine, such as Nicotrol®, and bupropion hydrochloride (commercially available as Zyban®); and steroids, including alclometasone dipropionate (commercially available as Aclovate®), betamethasone dipropionate (commercially available as Diprolene®), mometasone furoate (commercially available as Elocon®), fluticasone (commercially available as Flonase®, Flovent®, Flovent Diskus®, Flovent Rotadisk®), fluocinonide (commercially available as Lidex®), mometasone furoate monohydrate (commercially available as Nasonex®), desoximetasone (commercially available as Topicort®), clotrimazole/betamethasone dipropionate (commercially available as Lotrisone®), prednisolone acetate (commercially available as Pred Forte®, Prednisone®, Budesonide Pulmicort®, Rhinocort Aqua®), prednisolone sodium phosphate (commercially available as Pediapred®), desonide (commercially available as Tridesilon®), and halobetasol propionate (commercially available as Ultravate®).

Films of the present invention may further include agents useful for thyroid disease treatment, such as hormones TC and TD (commercially available as Armour Thyroid®); potassium deficiency treatment, including potassium chloride (commercially available as Micro-K®); triglycerides regulators, including omega-3-acid ethyl esters (commercially available as Omacor®); urinary medication, such as phenazopyridine hydrochloride (commercially available as Pyridium®) and methenamine, methylene blue/phenyl salicylate/benzoic acid/atropine sulfate/hyoscyamine (commercially available as Urised®); prenatal vitamins (commercially available as Advanced Natalcare®, Materna®, Natalins®, Prenate Advance®); weight control medication, including orlistat (commercially available as Xenical®) and sibutramine hydrochloride (commercially available as Meridia®).

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

In one particular method of forming a film, a wet film matrix is deposited onto the surface of a substrate. The substrate may have any length and width desired, depending on the size of the apparatus used to process the film. The length of the substrate is not critical, since the substrate may generally be fed into the film-forming apparatus on a continuous basis. The width of the substrate is sized to be fed into the apparatus used, and may vary as desired. The width of the substrate typically determines the width of the film product that can be prepared on that substrate. The most consistent drying is obtained with the substrate is only a few inches wider than the film being dried. It is typical then that the batch size determines the width of the film, which in turn determines the optimum width of the substrate. For experimental batches, the resulting dried film may only be 1 film strip wide, on the order of about 1 inch, which would require a width of substrate in the range of about 3 to about 7 inches. In some embodiments, the dried film may be from about 0.5 to about 2.5 inches in width, and the substrate may be about 1.5 to about 10 inches in width. Desirably, in such embodiments, the width of the substrate is about 1 to about 7 inches wider than the width of the dried film.

For larger commercial batches, such as where the optimum width of film would be sufficient to be packaged on formed on a multilane machine, the width of the dried film may be about 7.5 inches, and width of the substrate may be from about 9 to about 14 inches. In some embodiments, the width of the film may be from about 5 to about 10 inches, and the width of the substrate may be from about 7 to about 20 inches. In such large-scale batches, the width of the substrate is desirably from about 1 to about 10 inches wider than the width of the dried film. Larger batches are generally more efficient when coated at a typical multiple packaging machine width, including up to 4 individual films wide (i.e., 4 films, each having a width of about 5 to about 10 inches), or one film having a width of about 20 to about 30 inches. In such embodiments, it may be desired to use a substrate having a width of about 32 to about 40 inches.

A wet film-forming matrix is deposited onto the surface of a substrate. The matrix may be deposited in one layer, which is then capable of being cut into several smaller dosages. Alternatively, the matrix may be deposited such that it has a width that is equal to the desired width of the resulting film. In some embodiments, which will be discussed in further detail below, one embossed substrate may include several confined regions, into which a matrix may be deposited, thus forming several rows of formed film.

Once deposited on the surface of the substrate, the deposited matrix is dried through any desired drying means, including but not limited to those methods set forth in the patents and applications previously incorporated by reference above. One benefit of drying a film product on the surface of a substrate is that the film may be dried quickly and efficiently, resulting in a film that has a substantially flat form. Further, the film may become adhered to the surface of the substrate during drying, which aids in packaging and dispensing the end product. Any desired substrate may be used, including, for example, mylar, paper, plastic, metal, foil, and combinations thereof. The substrate may be laminated if desired. Further, the substrate may be chemically treated prior to depositing the wet film matrix thereon. Desirably, the substrate is substantially flat, but is flexible to allow for rolling. The substrate should be capable of being embossed or debossed, and capable of maintaining the embossed or debossed section over time.

Traditional methods of forming a film on a substrate have suffered difficulties in achieving uniformity of content. For example, as set forth in FIGS. 1A and 1B (Prior Art), a traditional method of forming a film on a non-embossed substrate is set forth. FIG. 1A depicts a wet film matrix that is initially deposited on the surface of a substrate, while FIG. 1B shows the difficulty in maintaining structural uniformity through such traditional methods. In such traditional methods, a substrate 2, having a substantially flat surface, is provided. A wet film matrix 4 is deposited onto the surface of the substrate 2. Any means to deposit the wet film matrix may be used, including coating, spraying, casting, extruding, and the like. As can be seen, when the wet film matrix 4 is initially deposited, the edges 6 of the matrix 4 are fairly perpendicular.

The perpendicular edges 6 of the matrix 4 have a film thickness that is approximately the same as the rest of the film matrix 4.

However, as the wet film matrix 4 sits on the substrate 2 over a period of time, even a relatively short period of time, gravity may alter the thickness and uniformity of the matrix 4. As can be seen in FIG. 1B, the edges 6' of the matrix 4 may "bleed out" the sides. When such matrix 4 is dried into the final film product, these edges 6' will have a resulting thickness that is not uniform with the rest of the film, and must be trimmed and discarded. Such discarding is wasteful, and may be expensive. Thus, the present invention provides a method for forming a film product on a substrate, while limiting or altogether eliminating such "bleed out" of the sides.

In one embodiment, the present invention provides a method of forming a film product using a substrate that is embossed (i.e., an "embossed substrate"). An embossed substrate of the present invention desirably has at least one confined region. In one particularly useful embodiment, the confined region of the substrate forms a channel defined by at least one embossed dam (also referred to as a "raised section"), that may be used to prevent the wet film matrix from bleeding out the side. As used herein, the term "confined region" refers to a channel formed in the embossed substrate, having first and second side walls along the longitudinal sides of the embossed substrate. It is preferred that the "confined region" not include a wall between the first and second side walls, but in some embodiments a wall between the first and second side walls may be used. Thus, the preferred configuration of the confined region is an uninterrupted channel, and not a well-type of region (which would have walls surrounding all sides). The confined region of the embossed substrate may be formed by embossing, depressing, debossing, or any desired means of forming a region confined by embossed dams or raised sections. As will be described in more detail below, the confined region may be formed by any methods desired, including mechanically pressing the substrate.

Figure 2B:
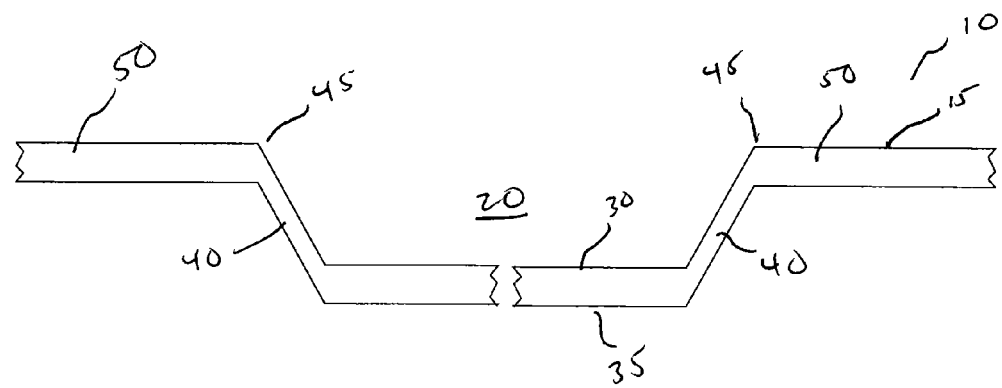
Figure 2C:
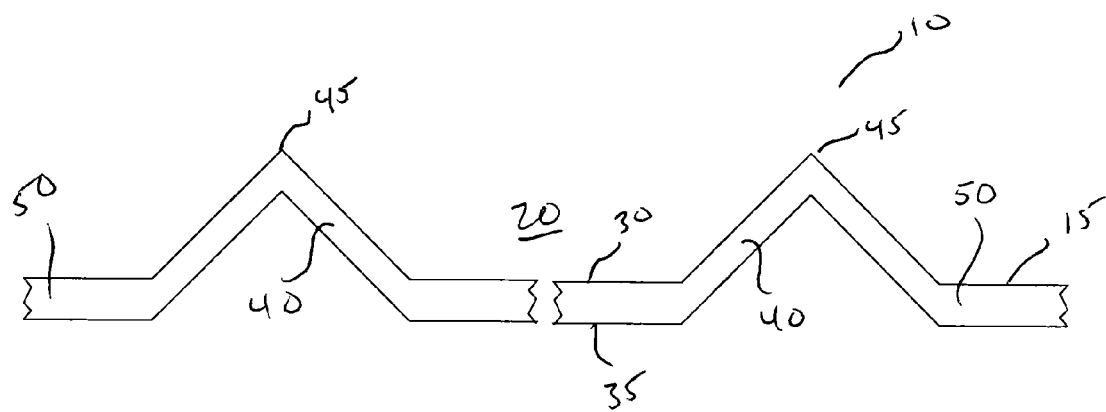
Figure 2D:
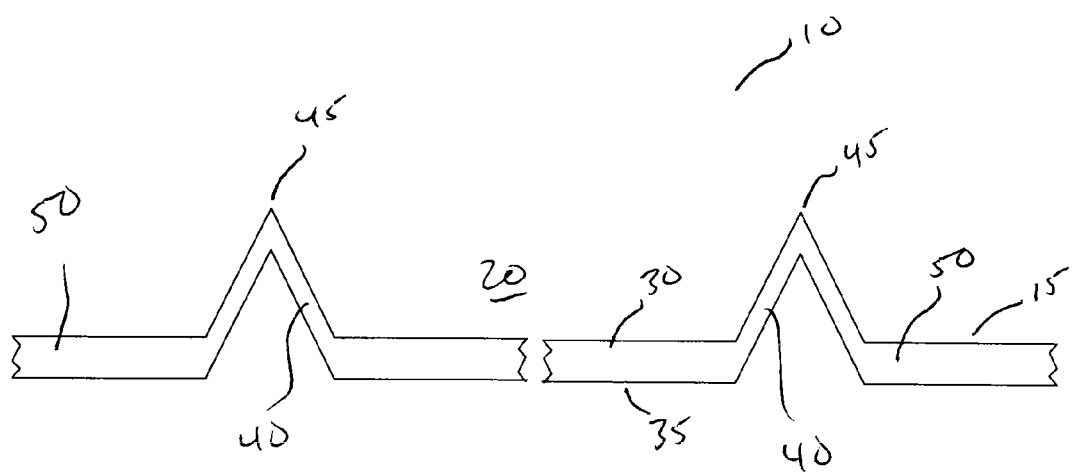
Figure 2E:
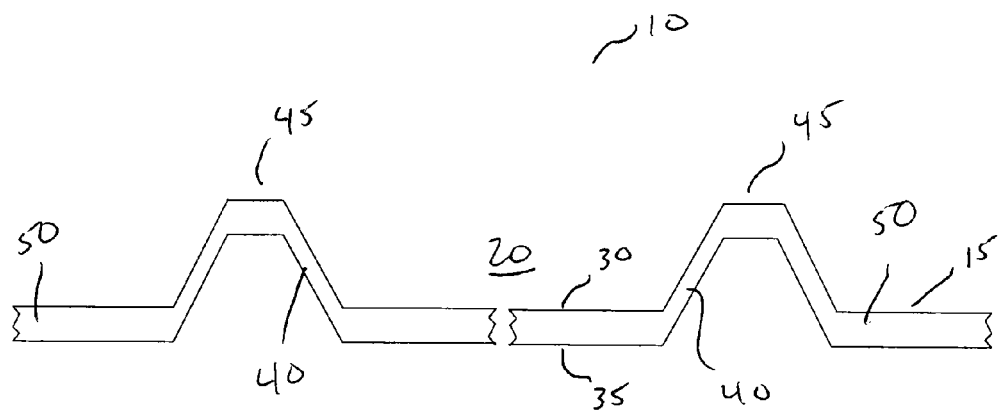
Figure 2F:
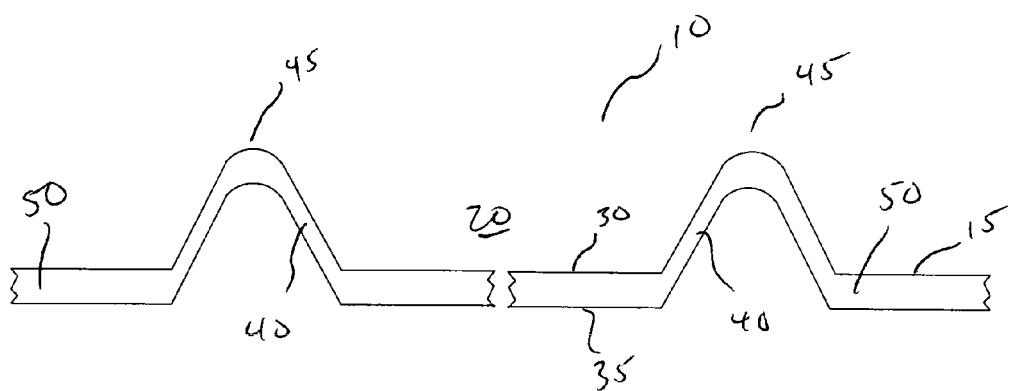

The present invention may be better understood through reference to the Figures, which generally set forth various embodiments of the present invention. With reference to FIGS. 2A-2F, various embossed substrates 10 are depicted. As can be seen, the embossed substrate includes at least one dam, which includes a side wall 40 and a side wall top 45. Any structural configuration for the dam may be used. For example, FIGS. 2A and 2B depict a dam that has a plateau configuration. FIGS. 2C and 2D depict a dam that has a peaked configuration. FIG. 2E depicts a dam that has a mesa configuration. FIG. 2F depicts a dam that has a mound configuration. As can be seen, each of the dam configurations have a side wall 40 that begins at the top surface 30 of the confined region 20 and ends at the side wall top 45. The side wall top 45 may be, of course, a peak, an angle, a curve, or a flat region, as desired. In any dam configuration, the dam (which includes the side wall 40 and side wall top 45) desirably has a height which is higher than the top surface 30 of the confined region 20. The use of a dam that is higher than the top surface 30 of the confined region 20 creates a channel where a wet film matrix may be deposited. As will be understood by those of skill in the art, FIGS. 2A-2F are intended to be representative of the present invention, and are not limiting to the particular embossed designs shown. Various alternative structures may be used that satisfy the present invention.

As explained above, substrates useful in the present invention are generally flat, having a generally flat top surface 15. A substrate may be embossed via any desired methods, including those described below, to provide an embossed substrate 10. The embossed substrate 10 includes at least one confined region 20. The confined region 20 may be any length and width desired, and will generally conform to the desired width of resulting film product to be formed. In one embodiment, the confined region 20 may be sized to the desired width of an individual film product. In an alternate embodiment, the confined region 20 may be sized larger than the width of one individual film product, so as to provide multiple film products. In this embodiment, the confined region 20 may be sized to about 30 inches in width, so as to form a film product having a width of 30 inches. This resulting film product may then be cut into individual film dosages having the desired width. Depending on the batch size and the optimum coating width for that batch size, the confined region 20 could be about 0.5 to about 3.0 inches wide for experimental batches, from about 5 to about 10 inches wide for small commercial batches, and from about 20 to about 30 inches wide for large commercial batches. Wider widths are contemplated, and are only limited by the size of the coating machine used in the process.

In yet another embodiment, one embossed substrate 10 may include a plurality of confined regions 20, so as to form a plurality of individual films having the desired width. One embossed substrate may include from one to about 30 confined regions 20, each confined region 20 having a width equal to the desired film width.

The confined region 20 includes a confined top surface 30 and a confined bottom surface 35. Desirably, the confined top surface 30 is generally flat, since the wet film matrix will be deposited onto the confined top surface 30. However, the confined top surface 30 may have markings or patterns thereon, which will create a marked or patterned film product. Further, so as to allow the embossed substrate 10 to be nested, the embossed bottom surface 35 is also desirably flat, and has a width that substantially conforms to the width of the confined top surface 30.

The confined region 20 is formed on at least one side by a side wall 40. The side wall 40 begins at a location on the confined top surface 30 and extends up to the side wall top 45. The confined region 20 thus has a thickness that may be measured from the confined top surface 30 to the side wall top 45. Desirably, the confined region 20 includes two side walls 40 that form a channel, but in some embodiments, only one side wall 40 may be used. The side wall 40 may be perpendicular to the confined top surface 30, or it may be angled. In one embodiment, the side wall 40 is substantially perpendicular, so as to form a resulting film product that has substantially perpendicular edges. It will be understood that the side wall 40 need not be exactly perpendicular, but may be substantially perpendicular to the confined top surface 30. How near to perpendicular the side wall 40 may be is a function of the strength of the material forming the embossed substrate. This is because, as closer to perpendicular the side wall 40 is, the thinner the embossed substrate 10 at the side wall 40 will be. A comparison of FIGS. 2A and 2B, for example, show this phenomenon. The side wall 40 of FIG. 2A has an angle that is less perpendicular to the confined top surface 30 than that in FIG. 2B. As can be seen, since the side wall 40 of FIG. 2B is more perpendicular, the embossed substrate 10 at the side wall 40 of FIG. 2B is thinner. The side wall 40 may have any angle with respect to the confined top surface 30, from substantially perpendicular (i.e. about 90 degrees) to about 145 degrees, and more particularly from about 100 degrees to about 145 degrees. In some embodiments, the side wall 40 (or side walls 40) may have an angle with respect to the confined top surface 30 of about 100 degrees, about 105 degrees, about 110 degrees, about 115 degrees, about 120 degrees, about 125 degrees, about 130 degrees, about 135 degrees, about 140 degrees, or about 145 degrees. In some instances, when a particularly viscous wet film matrix is used, the angle may be greater than 145 degrees. It is preferred that both side walls 40 have approximately similar angles with respect to the confined top surface 30, but they may have different angles if desired.

Although contemplated in the present invention, it is preferred to have a side wall 40 (or side walls 40) that is/are not perpendicular to the confined top surface 30. Having side walls 40 that are not perpendicular to the confined top surface 30 allow the embossed substrate to be able to nest with itself or another similar embossed substrate 10, allowing the user to keep the dry film rolled up in a uniform manner.

In order for the embossed substrate 10 to nest properly without any dry film attached thereon, the vertical thickness of the side wall 40 desirably does not exceed the vertical thickness of the unembossed portion of substrate 10. Such nesting would be desired, for example, when the embossed substrate 10 is rolled up waiting to be coated. If the substrate is to be nested within itself or a similar substrate, the vertical thickness of the side wall 40 should not exceed the combined thickness of the embossed substrate 10 and the dry film thickness 80.

The region of the embossed substrate 10 that is not within the confined region 20 will be referred to as the "outer region" 50. The outer region 50 may be any shape or width desired, and generally is sized to fit the apparatus used to deposit the wet film matrix and/or the apparatus used to dry the wet film matrix. In some embodiments, it may be desirable to have a wide outer region 50, which may aid in feeding the substrate into the film-forming apparatus. In other embodiments, it may be desirable to limit the size of the outer region 50, so as to maximize the film-forming potential of the embossed substrate 10. As explained above, the embossed substrate 10 may have a width that is from about 1 to about 10 inches wider than the confined region 20. Thus, the outer region 50 may have a width that is from about 1 to about 10 inches wider than the confined region 20. Thus, the outer region 50 on each side of the confined region 20 may have a width that is from about 0.5 to about 5 inches wider than the confined region 20. The outer regions 50 on each side of the confined region 20 may be the same or may be different from each other.

FIGS. 2A-2F depict various structures forming the embossed substrate 10. Again, such structures are representative only, and are not intended to limit the invention. In one embodiment referred to herein as a "plateau" configuration, the confined region 20 may be lower than the outer region 50 (FIGS. 2A and 2B). FIG. 2A shows side walls 40 having a large angle with respect to the confined top surface 30, while FIG. 2B shows side walls 40 having a smaller angle with respect to the confined top surface 30. Again, it is desired to use substantially perpendicular side walls 40. Such structure may be formed, for example, by embossing the substrate at the confined region 20 itself. FIGS. 2C and 2D show an alternate structure for the embossed substrate 10 having a "peaked" configuration. In this embodiment, the side walls 40 are raised in a peak-like form. FIGS. 2E and 2F show an alternate structure for the embossed substrate 10 having "mesa" and "mound" configurations respectively. The confined region 20 may be approximately the same height as the outer region 50, or the confined region 20 and outer region 50 may be different heights. FIG. 2C shows a peaked configuration having side walls 40 that have a large angle with respect to the confined top surface 30, while FIG. 2D shows a peaked configuration having side walls 40 that have a smaller angle with respect to the confined top surface 30.

Alternative structures may include, for example, the side walls 40 being substantially perpendicular to the confined top surface 30. In any configuration, however, it is desired that the embossed substrate 10 can be nested within itself or another similar embossed substrate 10.

Figure 3:
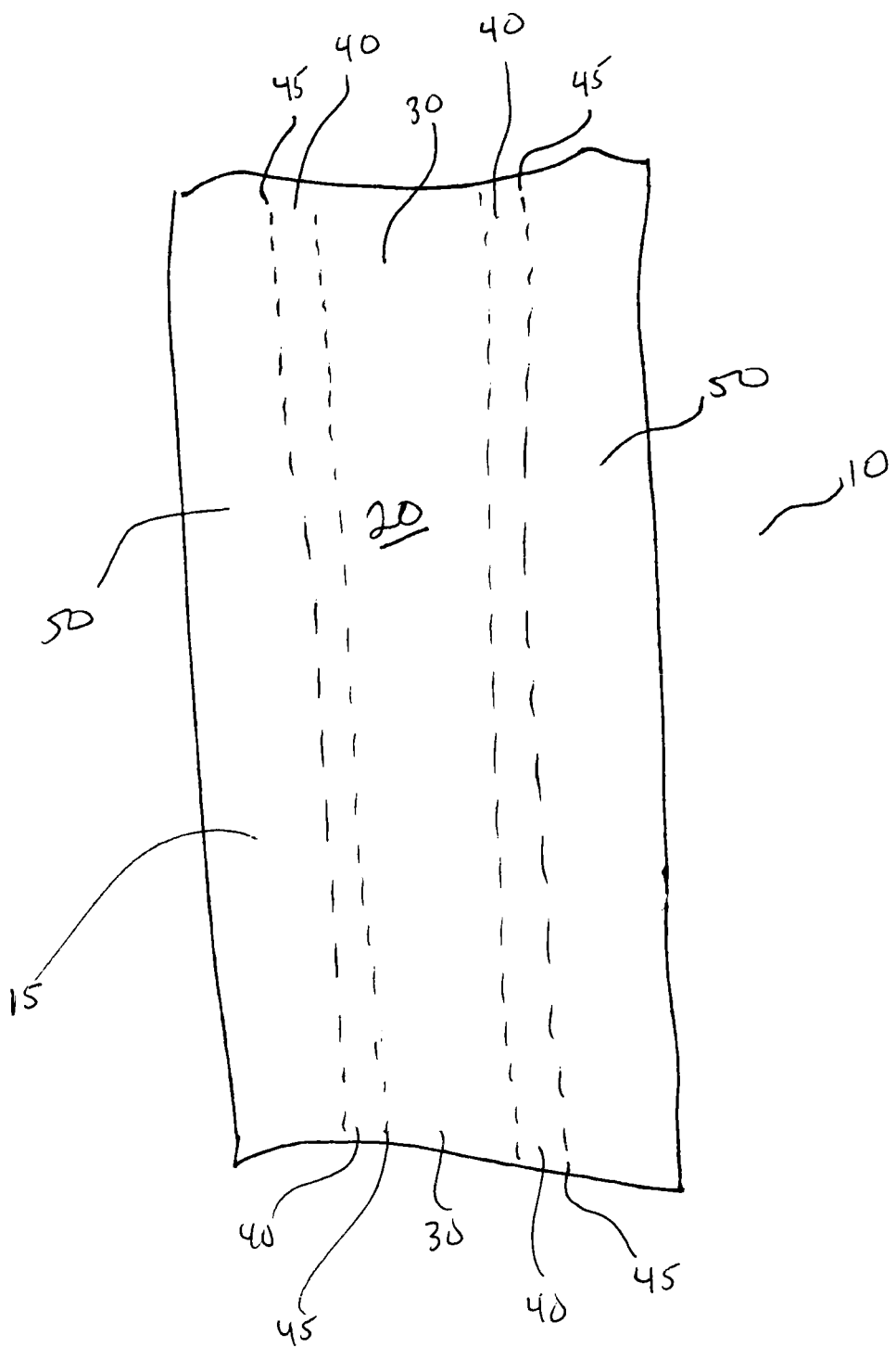
FIG. 3 is a top view of a substrate having an embossed section pursuant to the present invention.

As explained above, the embossed substrate 10 may have any width desired, and will generally conform to the size of the machinery used to form the film. FIG. 3 shows a top view of one embodiment of the embossed substrate 10. In this embodiment, the embossed substrate 10 includes one confined region 20, defined on its sides by two approximately parallel side walls 40. As explained above, the embossed substrate 10 may have more than one confined region 20, if desired. In an especially preferred embodiment, the confined region 20 does not have any dams or barriers perpendicular to the side walls 40, which allows for a continuous film formation along the length of the entire embossed substrate 10.

Figure 4A:
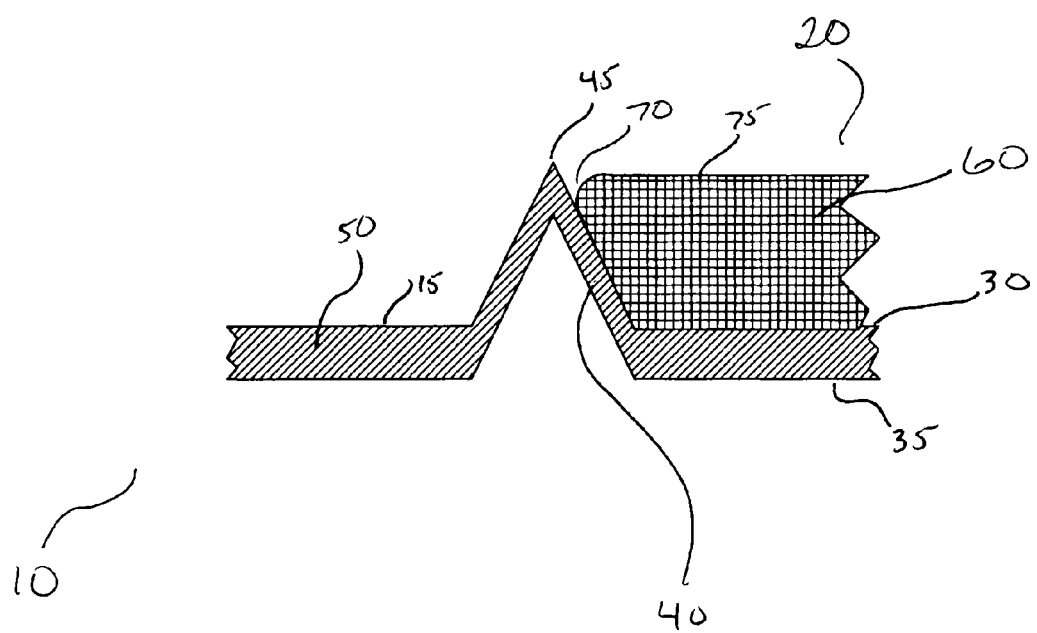
FIG. 4A is a cross-sectional view of a substrate with wet film thereon in accordance with the present invention.
Figure 4B:
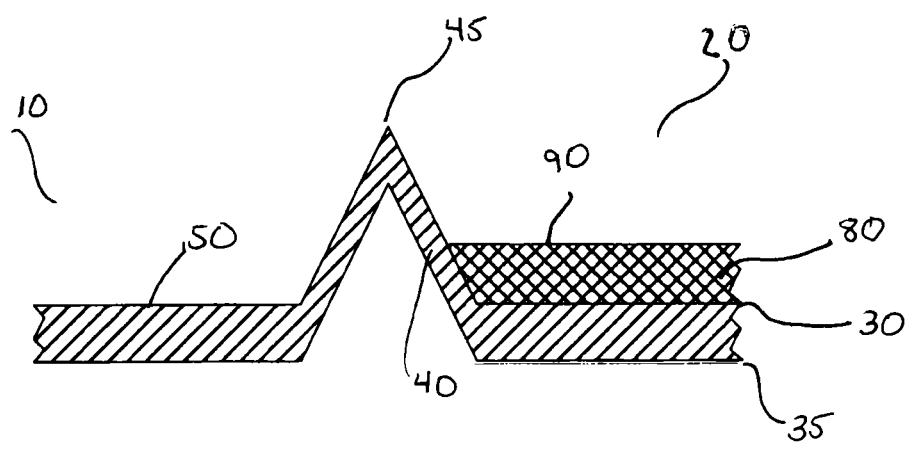
FIG. 4B is a cross-sectional view of a substrate with dried film thereon in accordance with the present invention.
Figure 5A:
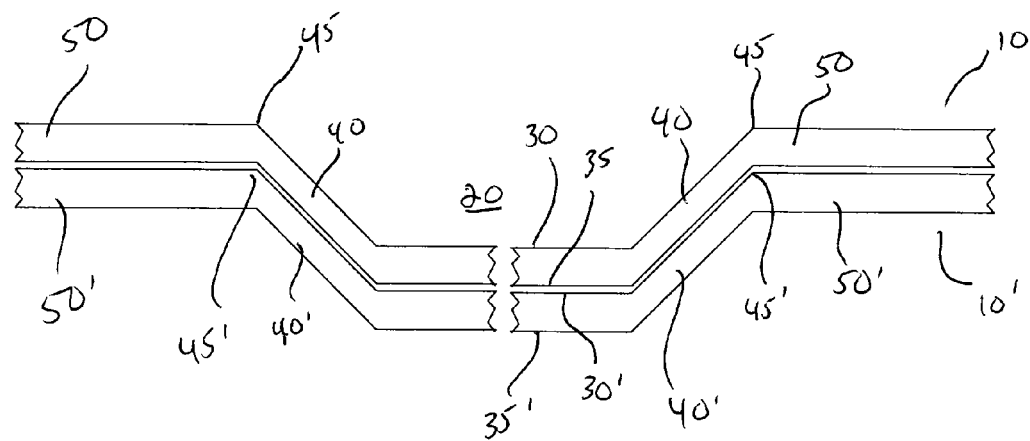
FIGS. 5A-5F depict various substrate dam formations in accordance with the present invention in nested form.
Figure 5B:
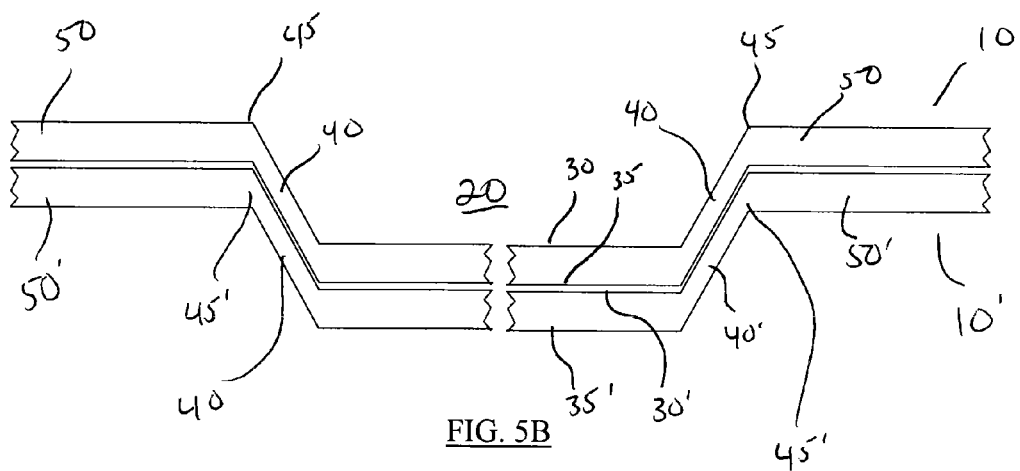
Figure 5C:
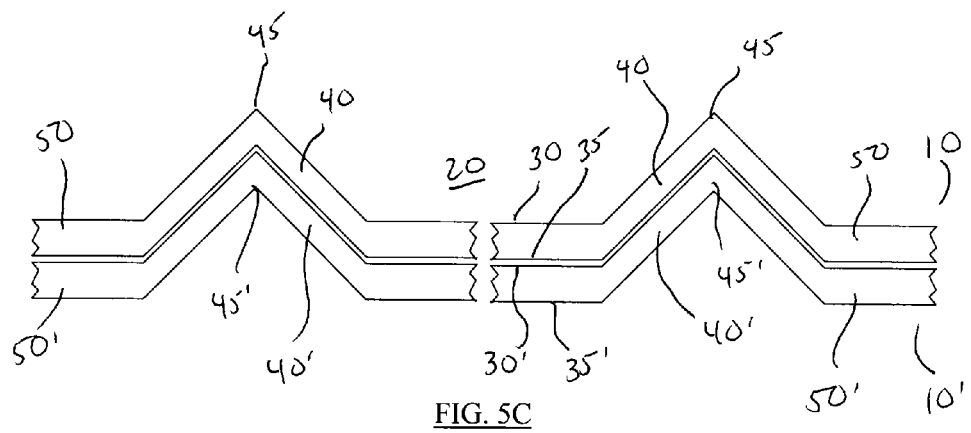
Figure 5D:
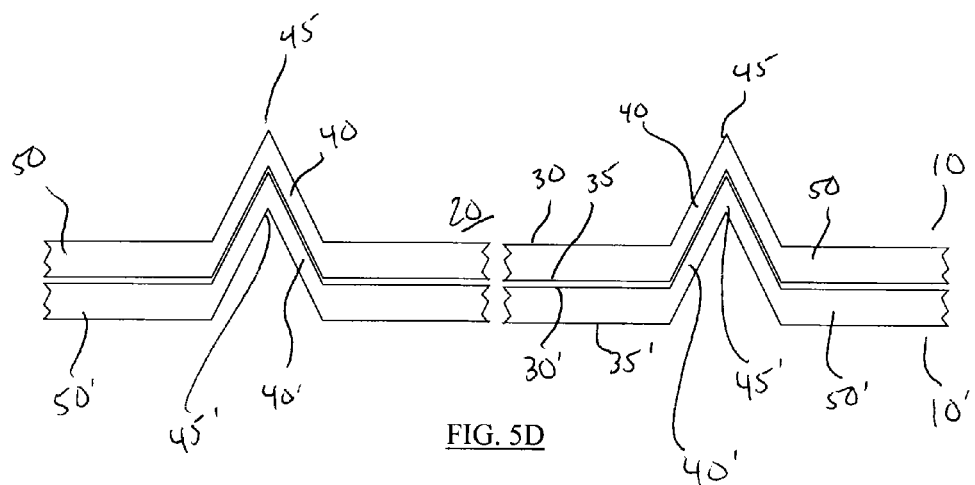
Figure 5E:
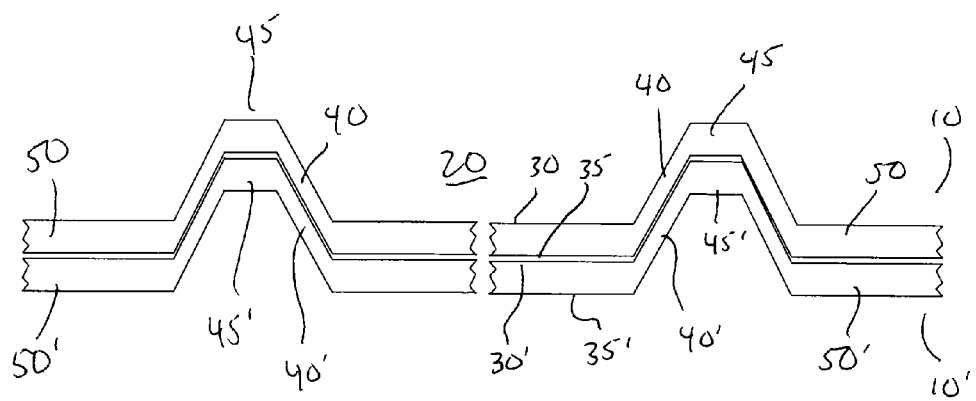
Figure 5F:
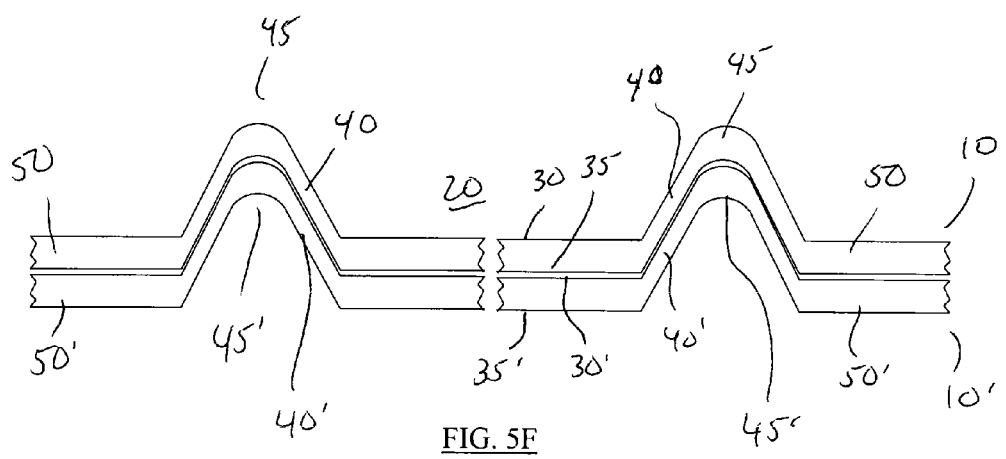

After the embossed substrate 10 has been formed, a wet film matrix may be deposited into the confined region 20 and onto the confined top surface 30. As explained above, the wet film matrix may then be dried via any desired means, thus forming the dried film. FIGS. 4A and 4B depict one embodiment of the formation of the film using a peaked dam configuration. FIG. 4A depicts the embossed substrate 10 after a wet film matrix 60 has been deposited thereon. FIG. 4A shows the embossed substrate 10 having a peaked dam configuration, but it will be understood that any embossed configuration may be used.

As can be seen, the embossed substrate 10 includes a confined region 20, which is defined by at least one side wall 40. A wet film matrix 60 may be deposited into the confined region 20 by any means desired, such that the wet film matrix 60 is deposited onto the confined top surface 30. The wet film matrix 60 may be deposited at any thickness desired (as measured from the confined top surface 30 to film surface 75), depending upon the desired thickness of the resulting dried film. Preferably, the top surface 75 of the wet film matrix 60 is equal to or lower than the side wall top 45. That is, the thickness of the wet film matrix 60 is preferably less than the thickness of the confined region 20 (as measured from the confined top surface 30 to the side wall top 45). In such embodiment, the side wall 40 acts as a barrier to hold the wet film matrix 60 in place, thus avoiding "bleed out" of the sides.

In some particularly useful embodiments, the wet film matrix 60 may be slightly thicker than the thickness of the confined region 20 (as measured from the confined top surface 30 to the side wall top 45). The ability of the wet film matrix 60 to have a thickness greater than the confined region 20 depends upon the viscosity and contact angle of the wet film matrix 60. If the viscosity and contact angle of the wet film matrix 60 is sufficiently high, the top surface 75 of the wet film matrix may be higher than the side wall top 45, without experiencing bleed out at the wet film corner 70. This embodiment may be particularly desired, as it may result in a dried film 80 that has a thickness approximately as thick as the confined region.

FIG. 4B depicts the dried film product. As can be seen, the dried film 80 has a thickness (as measured from the confined top surface 30 to dried film top surface 90) that is less than that of the wet film thickness (of FIG. 4A). This is due to the evaporation of solvents and other components of the wet film matrix 60 during the drying process.

Once the dried film 80 has been formed, the product may be finalized. As used herein, "finalized" refers to any steps taken after the film has been formed, including but not limited to cutting, sizing, printing on the film, packaging, distributing, administering, and combinations thereof. In some embodiments, the dried film is cut into individual strips and packaged. In other embodiments, the dried film 80 may be directly packaged. The dried film 80 may be removed from the substrate 10 prior to finalizing, or it may be finalized with the substrate 10.

In a preferred embodiment, the dried film 80 is stored for a period of time until it is ready to be packaged. Desirably, after the dried film 80 is formed, the embossed substrate 10 with dried film 80 is rolled upon itself, so as to minimize the space needed for storage.

In one particularly useful embodiment, the present invention provides an embossed substrate 10, which has a confined region 20 that is capable of being nested upon itself As used herein, the term "nested" refers to the ability of an confined region 20 (or regions 20) to be placed on top of another confined region 20 (or regions 20) in such a fashion that minimizes the space between congruent confined regions 20. FIGS. 5A-5F depict various structural arrangements of embossed substrates 10, which are capable of being nested. As can be seen, in each arrangement, the confined region 20 of a first substrate 10 fits within the confined region 20 of a second substrate 10'. It will be understood that the first substrate 10 and the second substrate 10' may be the same substrate, i.e., if the substrate is rolled upon itself. Alternatively, the first and second substrate (10, 10') may be separate substrates which are desired to be nested together. Desirably, the substrate 10 is capable of being nested upon itself prior to forming the dried film 80, which may aid in storing the embossed substrate 10 prior to use. In order for the embossed substrate 10 to nest without any film attached, the vertical thickness of the embossed side wall 40 should not exceed the vertical thickness of the unembossed portion of substrate 10 (i.e., the outer region(s) 50).

Figure 6:
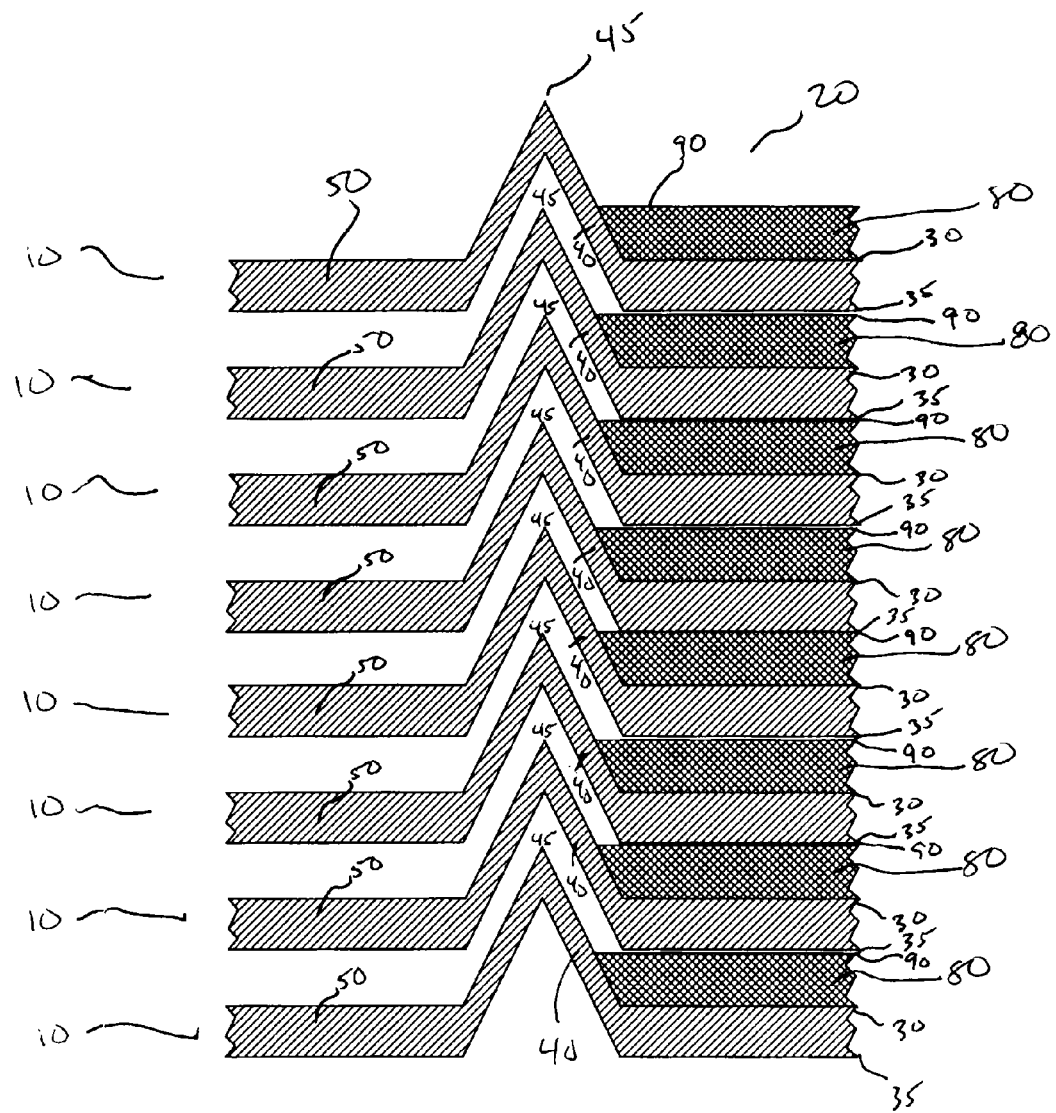
FIG. 6 is a cross-sectional view of nested film-containing substrates in accordance with the present invention.

Further, it may be desirable to use a substrate 10 that is capable of being nested after the dried film 80 has been formed. As may be seen in FIG. 6, a plurality of substrates 10, each having dried films 80 thereon, may be nested so as to minimize the space between substrates 10. Again, each substrate 10 may be separate or it may be one continuous substrate 10 that has been rolled upon itself. As can be seen, the dried film 80 is contained within the confined region 20 of each substrate 10. The dried film 80 is formed onto the confined top surface 30, and has a dried film top surface 90. The dried film top surface 90, when nested, is in communication with the embossed bottom surface 35. The side walls 40 and side wall tops 45 of the substrates 10 are capable of being nested, although they need not be in direct communication with each other. If the substrate is embossed as part of the coating process, then the vertical thickness of the side wall 40 should not exceed the combined thickness of the embossed substrate 10 and the dry film thickness 80

Nesting the substrates 10, both prior to forming the dried film 80 and after the dried film 80 has been formed thereon, has numerous advantages. First, the storage of nested substrates 10 is significantly lessened as compared to non-nested substrates 10. Further, nesting may be especially useful when the dried film 80 must be transported to a different location for final preparations, including, but not limited to, cutting, trimming, printing on the film surface, packaging, or other processes to finalize the film product for distribution. In embodiments where the substrate 10 is to be rolled upon itself for storage, it is desirable that the substrate 10 be made of a resilient material that is sufficiently flexible to allow for rolling without cracking or breaking. Similarly, it is desirable to use components to form a dried film 80 that is resilient enough to avoid cracking or breaking when rolled. Further, the material used for the substrate 10 should be capable of withstanding high temperatures, which may be used in the drying process.

Any method of forming the side walls 40 that define the confined region 20 may be used as desired. Typical methods for embossing substrate materials include, but are not limited to, extrusion, thermoforming, vacuum forming, cold forming, calender rolling, embossing rolls, and other methods known in the art. All of these methods are adaptable to the speeds at which the film forming and drying equipment runs. Such film forming and drying equipment runs are typically from about 1 to about 25 feet/minute.

The embossed substrate 10 may be formed in advance of forming the film. That is, the embossed substrate 10 may be formed prior to its used. In some embodiments, the confined region 20 of the substrate 10 may be formed during the process of forming the film.

Figure 7:
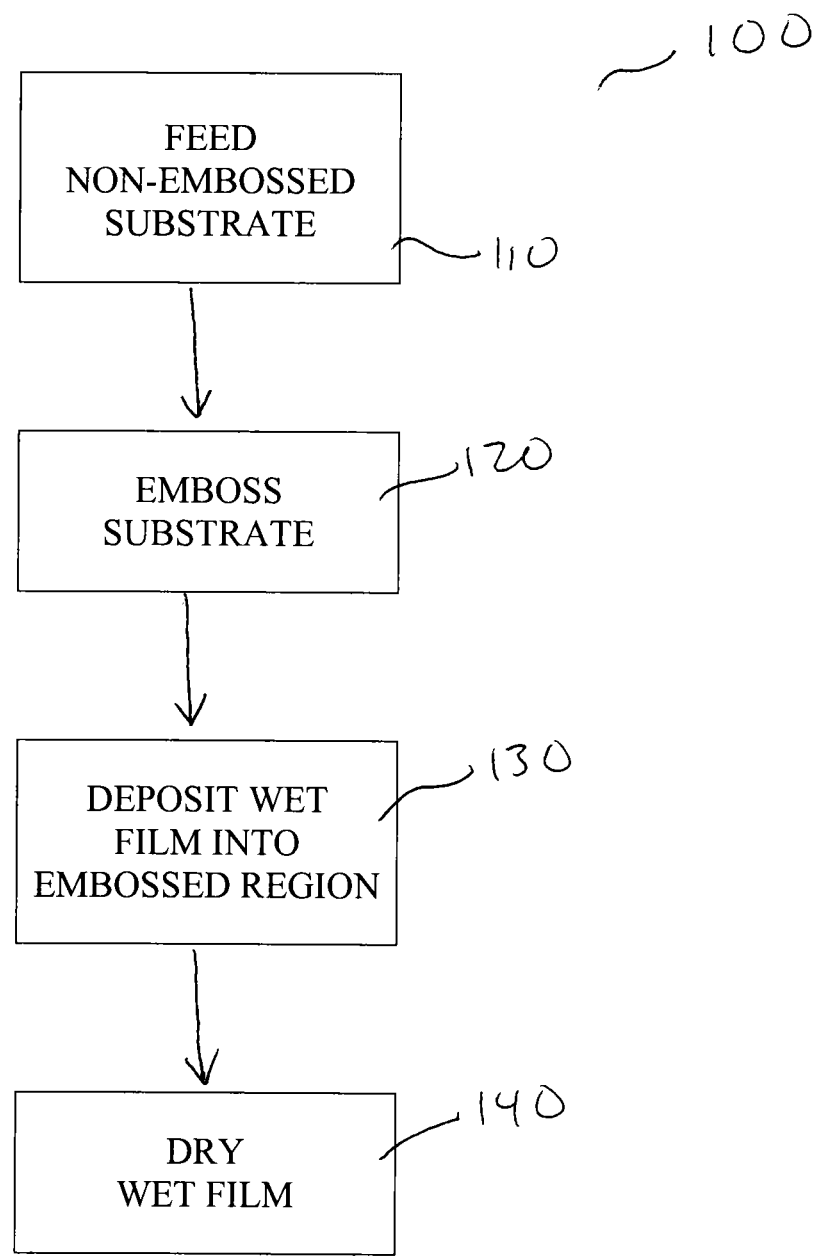
FIG. 7 is a flowchart depicting one method of forming a film using a substrate in accordance with the present invention.

One such method of forming a film product is set forth in FIG. 7. In this embodiment, a method 100 of forming a film is provided. In this method 100, the first step 110 includes providing a substrate that has not been embossed. The non-embossed substrate is then fed into a film-forming apparatus. The non-embossed substrate then undergoes the step 120 of entering an embossing apparatus. The embossing apparatus forms at least one confined region 20 into the non-embossed substrate, thus forming an embossed substrate 10. As explained above, any number of confined regions 20 may be formed into one embossed substrate 10.

Once the embossed substrate 10 has been formed, the step 130 of depositing a wet film matrix 60 onto the confined top surface 30 is performed. The step 130 of depositing the wet film matrix 60 may be performed immediately after the step 120 of embossing the substrate 10. Alternatively, the step 120 of embossing the substrate 10 may be performed in advance of the step 130 of depositing the wet film matrix 60, where the embossed substrate 10 is stored until it is ready to be used. The wet film matrix 60 may be any thickness desired, depending upon the desired thickness of the final dried film 80. Desirably, the thickness of the wet film matrix 60 is less than the thickness of the confined region 20 (as measured from the confined top surface 30 to the side wall top 45). Once the wet film matrix 60 has been deposited into the confined region 20, the embossed substrate 10 with deposited wet film matrix 60 is dried (step 140) to form the final dried film 80. As explained above, any drying method desired may be used.

Once the final dried film 80 is formed, it may be finalized for packaging and administration. Such finalization steps may include, for example, cutting the film, sizing the film, printing on the film, storing the film, packaging the film, administering the film, and combinations thereof. In one particularly useful embodiment, the finalization of the dried film 80 includes rolling the film 80 and substrate 10 and storing the rolled materials for future use.

The present invention therefore provides an embossed substrate 10 useful for the formation of a uniform film product, as well as various methods for forming the embossed substrate 10. The present invention further provides a method 100 of forming a film product using an embossed substrate 10. Variations to the particular embodiments set forth above are considered and are within the knowledge of those of ordinary skill in the art.

What is claimed is:

1. A method of forming a film product, comprising the steps of:
   a. Providing an embossed substrate having at least one confined region having a top surface and an outer region;

b. Depositing a wet film matrix comprising a medicament on said top surface of said confined region and excluding said wet film matrix from said outer region;
c. Drying said wet film matrix on said embossed substrate to form a dried film from which the medicament is mucosally absorbable: and
d. Finalizing said dried film;
wherein said dried film is adapted to be removed from the substrate prior to finalizing said dried film.

2. The method of claim 1, wherein said substrate comprises plastic, paper, mylar, foil, and combinations thereof.

3. The method of claim 1, wherein said confined region is defined on at least one side by a dam having a side wall.

4. The method of claim 1, wherein said confined region comprises a channel having a first side and a second side.

5. The method of claim 4, wherein said first side comprises a first dam and said second side comprise a second dam, said first and second dams each having a height which is higher than said top surface.

6. The method of claim 5, wherein said confined region has a depth defined by the distance between said top surface and the height of said first dam.

7. The method of claim 6, wherein said deposited wet film matrix has a depth substantially equal to the depth of said confined region.

8. The method of claim 6, wherein said deposited wet film matrix has a depth less than the depth of said confined region.

9. The method of claim 6, wherein said deposited wet film matrix has a depth higher than the depth of said confined region.

10. The method of claim 5, wherein said first dam comprises a peaked configuration.

11. The method of claim 5, wherein said first dam comprises a plateau configuration.

12. The method of claim 5, wherein said first dam comprises a mesa configuration.

13. The method of claim 5, wherein said first dam comprises a mound configuration.

14. The method of claim 1, wherein said embossed substrate is capable of being rolled upon itself in such a manner that said confined region is nested within itself.

15. The method of claim 1, wherein mucosally absorbable means absorbable through the oral, buccal, sublingual, vaginal, ocular, or anal areas of the body or though the tongue.

16. The method of claim 1, wherein said finalizing said dried film is selected from the group consisting of cutting said dried film, sizing said dried film, printing on said dried film, packaging said dried film, distributing said dried film, administering said dried film, and combinations thereof.

17. The method of claim 1, wherein said finalizing said dried film is packaging said dried film.

18. A method of forming a film product, comprising the steps of:
a. Providing a non-embossed substrate;
b. Embossing said non-embossed substrate to provide an embossed substrate having at least one confined region having a top surface and an outer region;
c. Depositing a wet film matrix comprising a medicament on said top surface of said confined region and excluding said wet film matrix from said outer region;
d. Drying said wet film matrix on said embossed substrate to form a dried film from which the medicament is mucosally absorbable; and
e. Finalizing said dried film;
wherein said dried film is adapted to be removed from the substrate prior to finalizing said dried film.

19. The method of claim 18, wherein said substrate comprises plastic, paper, mylar, foil, and combinations thereof.

20. The method of claim 18, wherein said step of embossing said non-embossed substrate comprises a step selected from the group consisting of extrusion, thermoforming, vacuum forming, cold forming, calender rolls, embossing rolls, and combinations thereof.

21. The method of claim 18, wherein said confined region is defined on at least one side by a dam having a side wall.

22. The method of claim 18, wherein said confined region comprises a channel having a first side and a second side.

23. The method of claim 22, wherein said first side comprises a first dam and said second side comprise a second dam, said first and second dams each having a height which is higher than said top surface.

24. The method of claim 23, wherein said confined region has a depth defined by the distance between said top surface and the height of said first dam.

25. The method of claim 24, wherein said deposited wet film matrix has a depth substantially equal to the depth of said confined region.

26. The method of claim 24, wherein said deposited wet film matrix has a depth less than the depth of said confined region.

27. The method of claim 24, wherein said deposited wet film matrix has a depth higher than the depth of said confined region.

28. The method of claim 23, wherein said first dam comprises a peaked configuration.

29. The method of claim 23, wherein said first dam comprises a plateau configuration.

30. The method of claim 23, wherein said first dam comprises a mesa configuration.

31. The method of claim 23, wherein said first dam comprises a mound configuration.

32. The method of claim 18, wherein said embossed substrate is capable of being rolled upon itself in such a manner that said confined region is nested within itself.

33. The method of claim 18, wherein mucosally absorbable means absorbable through the oral, buccal, sublingual, vaginal, ocular, or anal areas of the body or though the tongue.

34. The method of claim 18, wherein said finalizing said dried film is selected from the group consisting of cutting said dried film, sizing said dried film, printing on said dried film, packaging said dried film, distributing said dried film, administering said dried film, and combinations thereof.

35. The method of claim 18, wherein said finalizing said dried film is packaging said dried film.

36. A method of continuously forming a film product, comprising the steps of:
a. Providing a non-embossed substrate having a starting edge;
b. Feeding said starting edge of said non-embossed substrate into a film-forming mechanism, such that said non-embossed substrate continuously moves through said film-forming mechanism;
c. Continuously embossing said non-embossed substrate as it moves through said film-forming mechanism to provide an embossed substrate having at least one confined region having a top surface and an outer region;
d. Continuously depositing a wet film matrix comprising a medicament on said top surface of said confined region and excluding said wet film matrix from said outer region as said embossed substrate moves through said film-forming mechanism;

e. Drying said wet film matrix on said embossed substrate to form a dried film from which the medicament is mucosally absorbable: and f. Finalizing said dried film;

wherein said dried film is adapted to be removed from the substrate prior to finalizing said dried film.

37. The method of claim 36, wherein said substrate comprises plastic, paper, mylar, foil, and combinations thereof.

38. The method of claim 36, wherein said step of embossing said non-embossed substrate comprises a step selected from the group consisting of extrusion, thermoforming, vacuum forming, cold forming, calender rolls, embossing rolls.

39. The method of claim 36, wherein said confined region is defined on at least one side by a dam having a side wall.

40. The method of claim 36, wherein said confined region comprises a channel having a first side and a second side.

41. The method of claim 40, wherein said first side comprises a first dam and said second side comprise a second dam, said first and second dams each having a height which is higher than said top surface.

42. The method of claim 41, wherein said confined region has a depth defined by the distance between said top surface and the height of said first dam.

43. The method of claim 42, wherein said deposited wet film matrix has a depth substantially equal to the depth of said confined region.

44. The method of claim 42, wherein said deposited wet film matrix has a depth less than the depth of said confined region.

45. The method of claim 42, wherein said deposited wet film matrix has a depth higher than the depth of said confined region.

46. The method of claim 41, wherein said first dam comprises a peaked configuration.

47. The method of claim 41, wherein said first dam comprises a plateau configuration.

48. The method of claim 36, wherein said embossed substrate is capable of being rolled upon itself in such a manner that said confined region is nested within itself.

49. The method of claim 36, wherein mucosally absorbable means absorbable through the oral, buccal, sublingual, vaginal, ocular, or anal areas of the body or though the tongue.

50. The method of claim 36, wherein said finalizing said dried film is selected from the group consisting of cutting said dried film, sizing said dried film, printing on said dried film, packaging said dried film, distributing said dried film, administering said dried film, and combinations thereof.

51. The method of claim 36, wherein said finalizing said dried film is packaging said dried film.

* * * * *

UNITED STATES PATENT AND TRADEMARK OFFICE
CERTIFICATE OF CORRECTION

PATENT NO. : 8,956,685 B2  Page 1 of 1
APPLICATION NO. : 12/711883
DATED : February 17, 2015
INVENTOR(S) : Beuford A. Bogue et al.

It is certified that error appears in the above-identified patent and that said Letters Patent is hereby corrected as shown below:

Specification

At column 21, line 14, replace "of an confined region" with -- of a confined region --.

At column 22, line 15, replace "prior to its used" with -- prior to its use --.

Claims

At column 23, Claim 5, line 2, replace "second side comprise a second" with -- second side comprises a second --.

At column 24, Claim 23, line 2, replace "second side comprise a second" with -- second side comprises a second --.

At column 25, Claim 41, line 2, replace "second side comprise a second" with -- second side comprises a second --.

Signed and Sealed this
Twenty-fifth Day of August, 2015

Michelle K. Lee
*Director of the United States Patent and Trademark Office*